(12) United States Patent
Biermann et al.

(10) Patent No.: US 11,331,428 B2
(45) Date of Patent: May 17, 2022

(54) CASSETTE FOR A FLOW CONTROL APPARATUS

(71) Applicant: KPR U.S., LLC, Mansfield, MA (US)

(72) Inventors: Wayne Biermann, St. Charles, MO (US); Paul Trelford, St. Louis, MO (US); Kenneth M. Breitweiser, Brighton, IL (US); Daniel Schnettgoecke, O'Fallon, MO (US)

(73) Assignee: KPR U.S., LLC, Mansfield, MA (US)

( * ) Notice: Subject to any disclaimer, the term of this patent is extended or adjusted under 35 U.S.C. 154(b) by 410 days.

(21) Appl. No.: 16/280,883

(22) Filed: Feb. 20, 2019

(65) Prior Publication Data

US 2019/0388618 A1 Dec. 26, 2019

Related U.S. Application Data

(60) Provisional application No. 62/688,872, filed on Jun. 22, 2018.

(51) Int. Cl.
 *A61M 5/168* (2006.01)
 *A61M 5/142* (2006.01)
 *A61M 39/22* (2006.01)

(52) U.S. Cl.
 CPC .... *A61M 5/16881* (2013.01); *A61M 5/14232* (2013.01); *A61M 39/223* (2013.01);
 (Continued)

(58) Field of Classification Search
 CPC ............ A61M 5/1413; A61M 5/14232; A61M 5/16881; A61M 39/223; A61M 2039/226;
 (Continued)

(56) References Cited

U.S. PATENT DOCUMENTS 5,364,364 A   11/1994 Kasvikis et al.
5,540,668 A * 7/1996 Wilson, Jr. .......... A61M 39/223
                                              604/248

(Continued)

FOREIGN PATENT DOCUMENTS

EP     2221084 A1    8/2010
WO    9640328 A2   12/1996
(Continued)

*Primary Examiner* — Nathan R Price
*Assistant Examiner* — Justin L Zamory
(74) *Attorney, Agent, or Firm* — ArentFox Schiff LLP

(57) ABSTRACT

A pump set for use with a pumping apparatus includes tubing for carrying a liquid. A valve mechanism is mounted to the tubing between an inlet section and a pump engagement section. The valve mechanism includes a first port connected to the inlet section of the tubing, a second port connected to the pump engagement section of the tubing, and a valve disposed between the first and second ports. The valve includes a stem rotatably mounted within a stem holder. The stem includes a flow passage extending through the stem and having an open V shape whereby a narrow open end of the flow passage communicates with the first port and a wide open end of the flow passage communicates with the second port to place the inlet section of the tubing in communication with the pump engagement section of the tubing.

36 Claims, 31 Drawing Sheets

(52) U.S. Cl.
CPC . *A61M 2039/226* (2013.01); *A61M 2205/128* (2013.01); *A61M 2206/20* (2013.01)

(58) Field of Classification Search
CPC ........ A61M 2205/128; A61M 2205/12; A61M 2205/121; F16K 11/16; F16K 5/0407; Y10T 137/86823; Y10T 137/86871
See application file for complete search history.

(56) References Cited

U.S. PATENT DOCUMENTS

| | | | |
|---|---|---|---|
| 5,807,312 | A | 9/1998 | Dzwonkiewicz |
| 2005/0267439 | A1 | 12/2005 | Harr et al. |
| 2010/0211022 | A1* | 8/2010 | Harr .................... A61M 39/223 604/248 |
| 2014/0261808 | A1* | 9/2014 | Brouwer ............... F16K 39/024 137/625 |
| 2015/0018780 | A1 | 1/2015 | Butterfield et al. |
| 2015/0065988 | A1* | 3/2015 | Holderle ........... A61M 5/16886 604/500 |
| 2016/0015885 | A1 | 1/2016 | Pananen et al. |
| 2018/0296820 | A1 | 10/2018 | Bogoslofski et al. |

FOREIGN PATENT DOCUMENTS

| | | |
|---|---|---|
| WO | 2009029751 A1 | 3/2009 |
| WO | 2011025589 A1 | 3/2011 |

\* cited by examiner

CASSETTE FOR A FLOW CONTROL APPARATUS

CROSS-REFERENCE TO RELATED APPLICATION

This application is the nonprovisional application of U.S. Provisional Application Ser. No. 62/688,872 filed Jun. 22, 2018, the entirety of which is incorporated by reference.

FIELD OF THE INVENTION

The present invention generally relates to a flow control system with a flow control apparatus and a feeding set, and more particularly to a cassette for use with the flow control apparatus.

BACKGROUND OF THE INVENTION

Administering medicine or nutrition to a patient who cannot intake the medicine or nutrition orally can be effected by utilizing peristaltic flow control systems. Typically in such systems, fluid is delivered to the patient by a pump set including a flexible elastomeric tubing loaded on a flow control apparatus, such as a peristaltic pump, which delivers fluid to the patient at a controlled rate of delivery. The peristaltic pump usually has a housing that includes a rotor operatively engaged to a motor through a gearbox. The rotor drives fluid through the flexible tubing of the pump set by the peristaltic action effected by reversible compression created by impingement, e.g., pinching, by one or more roller on the rotor. Rotation of the rotor progressively compresses the elastomeric tubing that drives the fluid at a controlled rate. The pump set may have a valve mechanism for permitting or preventing fluid flow through the pump set. The flow control system may also have a controller that operatively regulates the one or more motors which effectively controls fluid flow.

Peristaltic pumps operate by delivering fluid in small charges called "aliquots". The rotor engages elastomeric tubing of the pump set, pinching off a portion of the elastomeric tubing and pushing fluid forward of the pinch point, e.g., closer to the patient than to the source of fluid toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally accurate, and therefore very useful in the administration of medication and therapeutic fluids to the patient.

SUMMARY

In one aspect, a pump set for use with a pumping apparatus generally comprises tubing for carrying a liquid. The tubing comprising an inlet section for connection to a liquid source and a pump engagement section configured for engagement by the pumping apparatus to pump the liquid through the tubing. A valve mechanism attached to the tubing between the inlet section and the pump engagement section comprises a first port connected to the inlet section of the tubing, a second port connected to the pump engagement section of the tubing, and a valve disposed between the first and second ports. The valve includes a rotatable stem to selectively communicate the first port with the second port. The stem includes a flow passage extending through the stem from an inlet end of the flow passage to an outlet end of the flow passage whereby the inlet end of the flow passage communicates with the first port and the outlet end of the flow passage communicates with the second port to place the inlet section of the tubing in communication with the pump engagement section of the tubing. The flow passage increases in cross-sectional area from the inlet end toward the outlet end.

In another aspect a fitting assembly for use in a cassette configured for attachment to a pumping apparatus generally comprises a first port, a second port, and a valve disposed between the first and second ports. The valve includes a stem rotatably mounted to selectively communicate the first port with the second port. The stem includes a flow passage extending through the stem from an inlet end of the flow passage to an outlet end of the flow passage whereby the inlet end of the flow passage communicates with the first port and the outlet end of the flow passage communicates with the second port to place the inlet section of the tubing in communication with the pump engagement section of the tubing, the flow passage increasing in cross-sectional area from the inlet end toward the outlet end.

In yet another aspect, cassette for use with a pumping apparatus generally comprises a body configured for releasable attachment to the pumping apparatus to mount the cassette to the pumping apparatus, and a fitting releasably mountable to the body. The fitting including a valve mechanism comprising a first port, a second port, and a valve disposed between the first and second ports. The valve includes a stem rotatably mounted to selectively communicate the first port with the second port. The stem including a flange configured for engagement with a catch on the pumping apparatus to secure the fitting to the pumping apparatus when the stem is rotated to communicate the first port with the second port In still another aspect, a cassette for use with a pumping apparatus generally comprises a body configured for releasable attachment to the pumping apparatus to mount the cassette to the pumping apparatus. The body comprises a front, a back, a top, a bottom, and a curved guide wall extending downward from the top of body. A fitting is mounted on the body. The fitting has an inlet port for attaching inlet tubing to the cassette and an outlet port for attaching outlet tubing to the cassette. The outlet port is recessed from the top of the body. The curved guide wall extends adjacent the outlet port of the fitting for supporting the outlet tubing to prevent kinking of the outlet tubing.

BRIEF DESCRIPTION OF THE DRAWINGS

Corresponding reference characters indicate corresponding parts throughout the drawings.

DETAILED DESCRIPTION

One or more aspects of the present invention pertain to peristaltic pumps such as rotary peristaltic pumps and particularly to rotary peristaltic pumps utilizing a cassette having a valve for selecting between a plurality of fluid flow configurations. The cassette also has a configuration for preventing an outlet tube attached to the cassette from kinking. Any one or more advantageous features or structures that provide or facilitate any one or more of such features may be implemented in a peristaltic pump employed in various commercial and industrial applications. Thus, although the detailed discussion is directed to an enteral feed pump with a cassette, any one or more features of the invention may be embodied or implemented in other peristaltic pumps, with or without a cassette. For example, although the exemplarily discussed pump is a rotary peristaltic enteral feeding pump, the present invention has application to other types of peristaltic pumps (not shown), including medical infusion pumps. The general construction and operation of the enteral feeding pump, except as set forth hereinafter, may be generally the same as disclosed in co-assigned U.S. Pat. No. 7,608,059 issued Oct. 27, 2009, entitled FLOW CONTROL APPARATUS; U.S. Pat. No. 7,092,797 issued Aug. 15, 2006, entitled FLOW MONITORING SYSTEM FOR A FLOW CONTROL APPARATUS; and U.S. Pat. No. 7,534,099 issued May 19, 2009, entitled ALIQUOT CORRECTION FOR FEEDING SET DEGRADATION, the disclosures of which are incorporated herein by reference. One or more of the various features and aspects of the invention may be implemented in peristaltic pumps that use mechanisms other than rollers without departing from the scope of the present invention such as linear peristaltic pumps. Moreover, although an exemplary feeding set 7 is shown, other types of pump sets (not shown) can be used without departing from the scope of the present invention.

Figure 1:
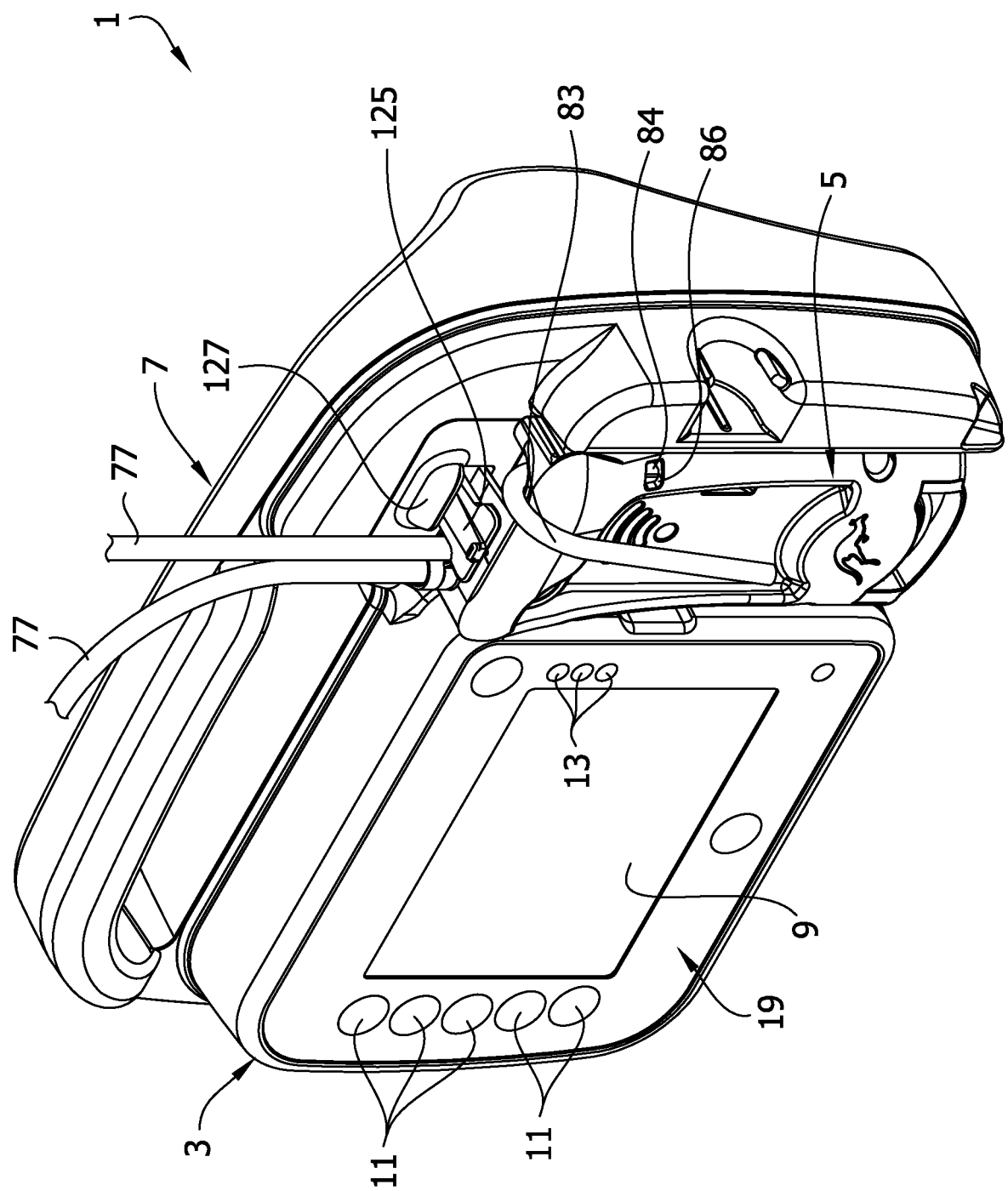
FIG. 1 is a perspective view of a feeding system with pumping apparatus and a fragmentary portion of a feeding set and a cassette.
Figure 2:
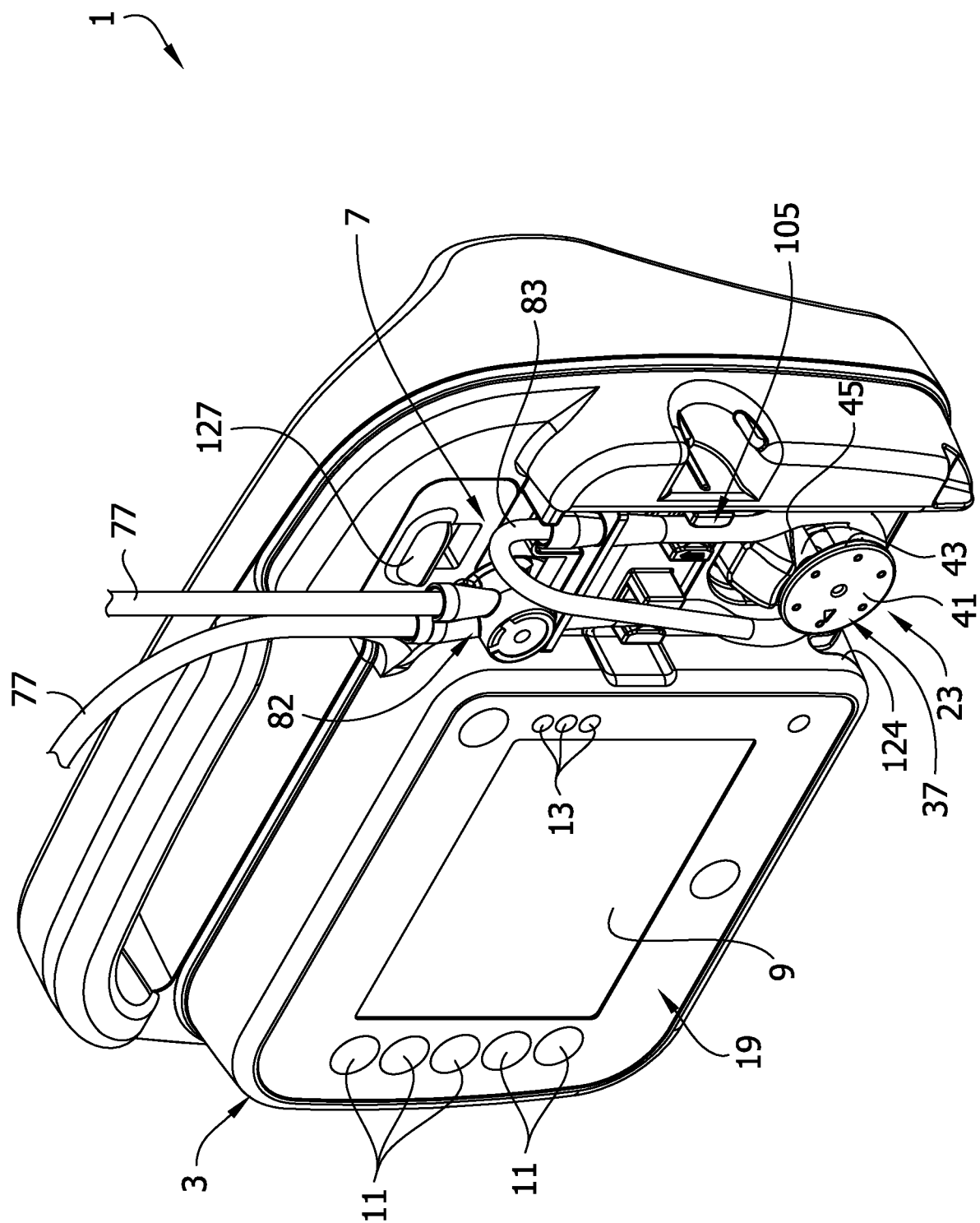
FIG. 2 is a perspective view of the system of FIG. 1 showing the pumping apparatus, but with portions of the cassette removed.
Figure 3:
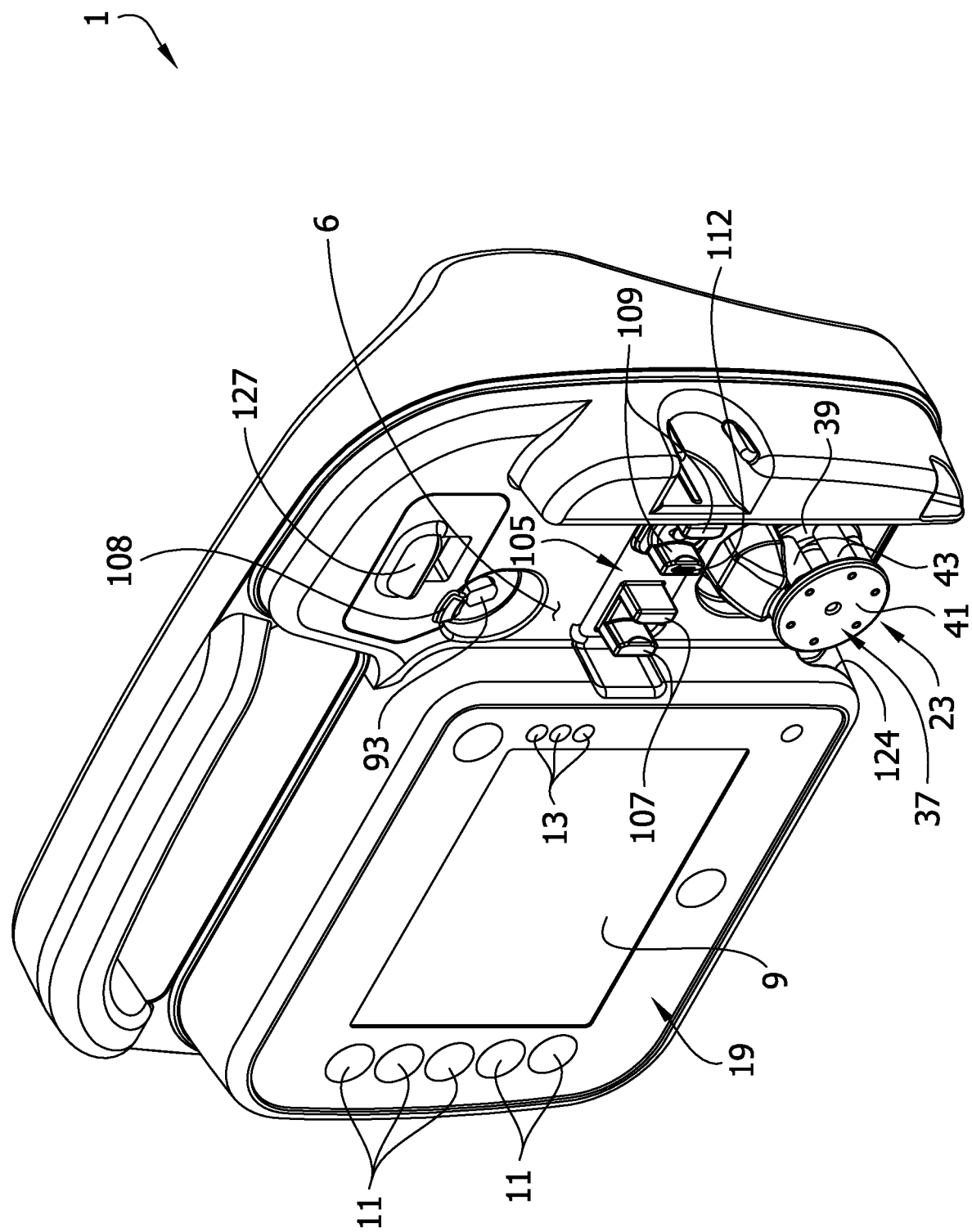
FIG. 3 is the perspective view of FIG. 1 without the feeding set and cassette.

Referring now to the drawings, and in particular FIGS. 1-3, an exemplary enteral feeding pump (broadly, "pumping apparatus") constructed according to the any one or more of the principles of the present invention is generally indicated at 1. The feeding pump may comprise a housing generally indicated at 3 that is constructed so as to mount a cassette, generally indicated at 5, and a feeding set (broadly, a "pump set"), a fragmentary portion generally indicated at 7, removably received in the cassette 5. The cassette 5 is releasably attachable to the housing 3. In the illustrated embodiment, the cassette 5 is removably received in a cassette recess 6 in the housing 3 (FIG. 3). It will be appreciated that "housing" as used herein may include many forms of supporting structures (not shown), including without limitation multi-part structures and structures that do not enclose or house the working components of the pump 1. In the illustrated embodiment, the pump 1 and pump set 7 form a "feeding system." Moreover, various aspects and features of the present invention can be implemented without the recess 6. The pump 1 may also have a display screen 9 on the housing 3 that is capable of displaying information about the status and operation of the pump. One or more buttons 11 which can be proximate the display screen 9 can be provided for use in controlling and obtaining information from the pump 1, and one or more light emitting diodes 13 can provide status information for the pump. Legs (not shown) may be disposed at the bottom of the housing 3 to support the housing so that the display screen 10 is angled slightly upward for ease of viewing by a user or operator.

The display screen 9 may be part of a front panel (generally indicated at 19) of the housing 3 and may be removably attached to the housing. The enteral feeding pump 1 may further include a pumping unit indicated generally at 23 comprising a pump motor (not shown) connected to a rotor shaft (not shown). A battery (not shown) may be received in the housing 3 for powering the pump motor. A power source other than or in addition to the battery could be used to energize the pump including one or more prime movers which drive the pumping unit through the rotor shaft.

The pumping unit 23 may include a rotor (generally indicated at 37) which can be coupled to the rotor shaft. The rotor 37 may include an inner disk 39, an outer disk 41, and four rollers 43 (only three of which are shown) mounted between the inner and outer disks for free rotation relative to the disks about their longitudinal axes (FIGS. 2 and 3). The rollers 43 engage a tube 45 (FIG. 2) of the feeding set 7 to deliver fluid through the feeding set 7 to a subject when the feeding set 7 is received in the cassette 5 and the cassette 5 is attached to the housing 3. Other numbers of rollers are also envisioned. For example, five or six rollers may also be used without departing from the scope of the disclosure.

Referring to FIGS. 4-7, the cassette 5 may comprise a cassette body 51 having a front 53, a back 55, a top 57, and a bottom 59. Side walls 61 and top wall 63 may extend from the back 55 of the cassette body 51 forming a back cavity configured for receiving a fitting 65. The tube 45 may be attached to the fitting 65. The fitting 65 may have tabs that allow the fitting 65 to be secured or snapped into the cassette. In some cases, the fitting can be removably secured to the cassette 5.

The fitting 65 can comprise a base 67, an inlet 69, an outlet 71, and a stem holder 66. The inlet 69 may include a first attachment portion 73 for insertion into an inlet end of the tube 45, and a pair of second attachment portions 75A, 75B for receiving inlet tubing 77 (FIG. 2). The outlet port 71 may include a first attachment portion 79 for engagement or attachment to, such as by insertion into an outlet end of the tube 45, and a second attachment portion 81 for attachment to, such as by receiving outlet tubing 83. An opening of the second attachment portion 81 that receives the outlet tubing 83 may funnel or taper down away from the opening to secure the tubing in the opening. The outlet tubing 83 may also be treated with a solvent to soften the tube for insertion into and bonding with the attachment portion 81. Second attachment portion 75A may be placed in fluid communication with a feeding source (e.g., nutrient liquid bag), and second attachment portion 75B may be placed in fluid communication with a flushing source (e.g., flushing fluid bag) via the inlet tubing 77. To aid in the identification of the preferred attachment of the fluid sources, second attachment portion 75A extends above second attachment portion 75B. Thus, a user can readily identify the taller second attachment portion 75A as the feeding source port. Alternatively, second attachment portion 75B could be attached to the feeding source and second attachment portion 75A could be attached to the flushing source.

The tube 45, fitting 65, inlet tubing 77, and outlet tubing 83 may comprise the pump set 7. It is also envisioned that the cassette 5 may be considered to be part of the pump set. In a preferred embodiment, the cassette 5 is made from a polymeric material such as polycarbonate.

Referring to FIGS. 8-13C, a stopcock 64 includes a cylindrical stem 68 received in a cylindrical receptacle 70 in the stem holder 66 of the fitting 65. The stem 68 is moveable (i.e. rotatable) in the opening 70 to selectively communicate the second attachment portions 75A, 75B with the first attachment portion 73 for placing the pump set in one of a fluid delivery configuration, a flushing configuration, or a fluid flow blocked configuration. The second attachment portions 75A, 75B each have outlets which communicate with the opening 70 in the fitting 65, and first attachment portion 73 has an inlet that communicates with the opening in the fitting. In one embodiment, the outlet of the second attachment portions 75A is non-uniformly circular-shaped to increase the outlet area without increasing the size of the stopcock 64. The exemplary oval-shaped outlet illustrated in FIG. 10A, for example, allows, for example, thicker and more viscous feeding solutions to be more readily fed into the pump set 7 without enlarging the stopcock. The stem 68 comprises a cylindrical body 72 having a first opening 74 (FIG. 11A) and a second opening 76 (FIG. 11B) formed in the body. The first opening 74 has a circular shape, and second opening 76 is elongate such that a first dimension of the opening 76 is greater than a second orthogonal dimension. In the illustrated embodiment, the second opening 76 has a longer slotted dimension than the diameter of the first opening 74. The first and second openings 74, 76 are located generally on opposite sides of the body 72 and are positioned such that they are in the same or substantially similar plane so that fluid flow through the stem 68 extends downward from the second attachment portions 75A, 75B to the first attachment portion 73 generally within a single plane (FIGS. 12 and 13A-C). More specifically, fluid may flow through the stem 68 along a single axis from the first opening 74 to the second opening 76. This increases the efficiency of the valve by providing a straight line flow path through the stem 68. In other embodiments, the configurations of openings 74, 76 could be reversed.

A flow passage 88 extends within the body 72 of the stem 68 from an inlet end at the first opening 74 to an outlet end at the second opening 76. The passage 88 widens, thereby increasing its cross sectional area from the first opening 74 to the second opening 76. The passage 88 may include curved inner walls 92 giving the passage roughly an inverted modified V-shaped configuration. The curved inner walls 92 define a first section 130 that widens at a generally constant rate from the first opening 74 to an end of the first section, and a second section 132 that widens at a non-constant rate from the first section 130 to an end of the second section 132. The rate at which the second section 132 widens increases toward the end of the second section 132. A third section 134 widens at a non-constant rate from the second section 132 to an end of the third section 134. The rate at which the third section 134 widens decreases toward the end of the third section. A fourth section 136 widens at a constant rate from the third section 134 to the second opening 76. Broadly, the stem 68 and stem holder 66 may be considered a valve mechanism.

The contour of the passage 88 provides benefits in the molding process of the stem 68. In particular, by forming the passage to have the modified 'V' shape, the thickness of the wall between the passage and cylindrical exterior surface of the stem 68 on each side can be kept smaller. A smaller wall thickness assists in maintaining a more consistently cylindrical shape of the exterior surface. This prevents deviations in the exterior surface of the stem 68 which can create gaps between the stem 68 and the stem holder 66 permitting fluid flow between the second attachment portions 75A, 75B when the stem 68 is in the fluid flow blocked position. To the contrary, a passage having a true 'V' shape (represented by the dashed lines in FIG. 12) can result in the thickness of the stem 68 around the passage 88, generally near the middle of the passage, that is too large to be produced in the molding process without causing inconsistencies in the circumference of the stem. However, by contouring the passage 88 to have one or more sections intermediate the inlet end (opening 74) and the outlet end (opening 76) increase more rapidly in width (an therefore cross sectional area), the maximum thickness of the wall is reduced to a thickness that will hold its shape in the molding process. Thus, the thickness of the wall of the stem 68 around the second, third, and fourth sections 132, 134, 136 is smaller than if the passage followed a standard 'V' profile. This smaller wall thickness allows the stem 68 to be molded without producing irregularities in the outer circumference of the stem 68.

Figure 11A:
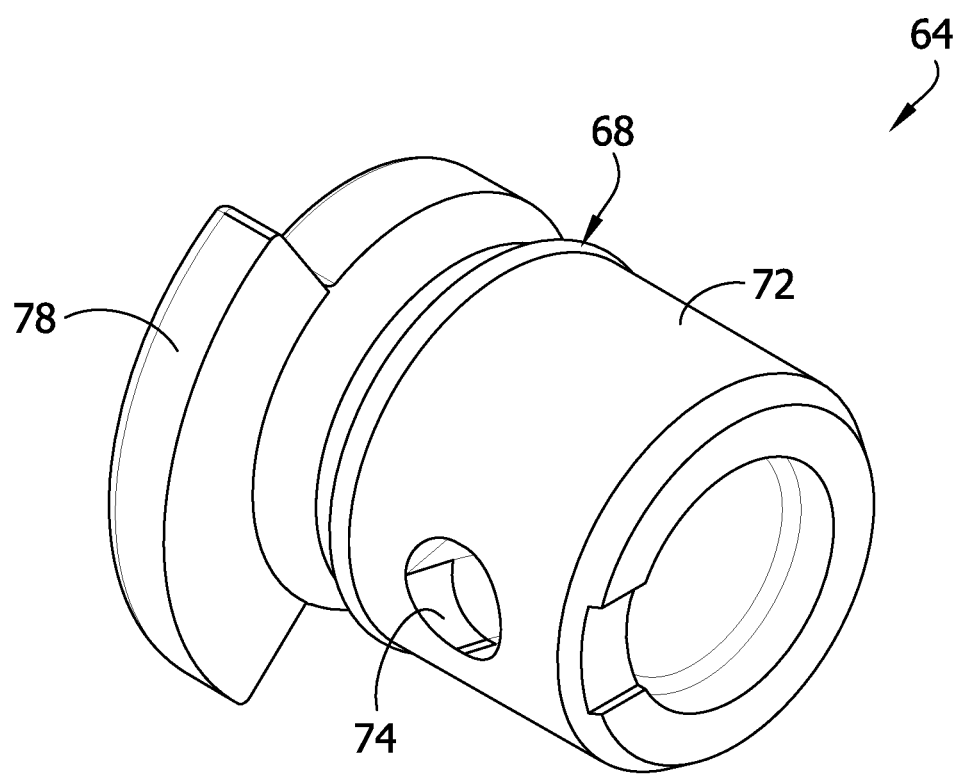
FIG. 11A is a rear and side perspective view of the stem.
Figure 11B:
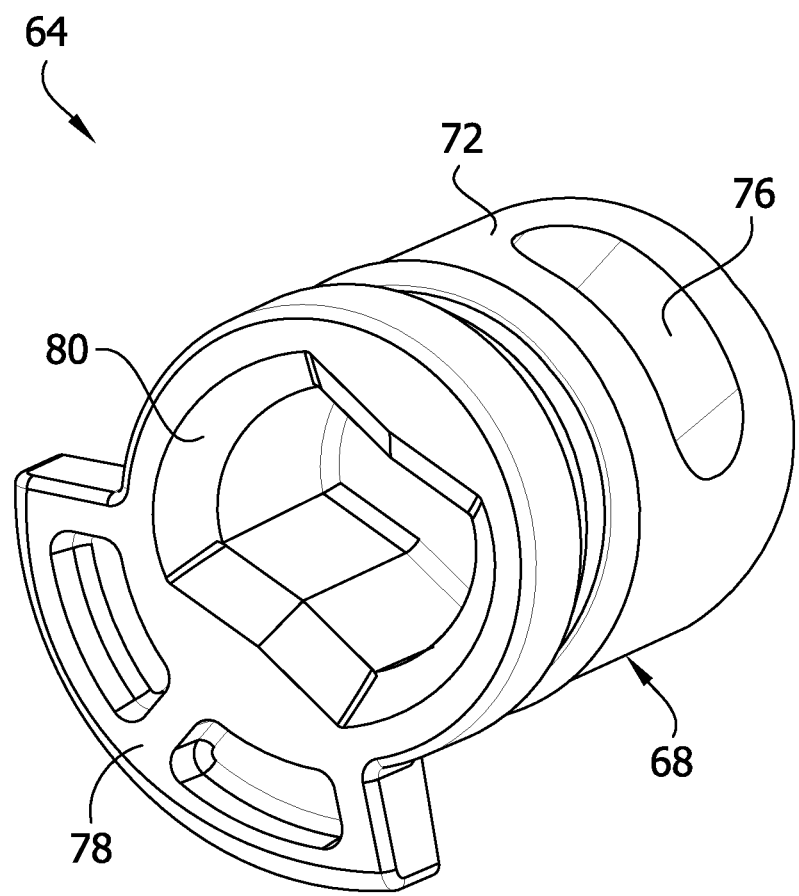
FIG. 11B is a front and side perspective view of the stem.
Figure 11C:
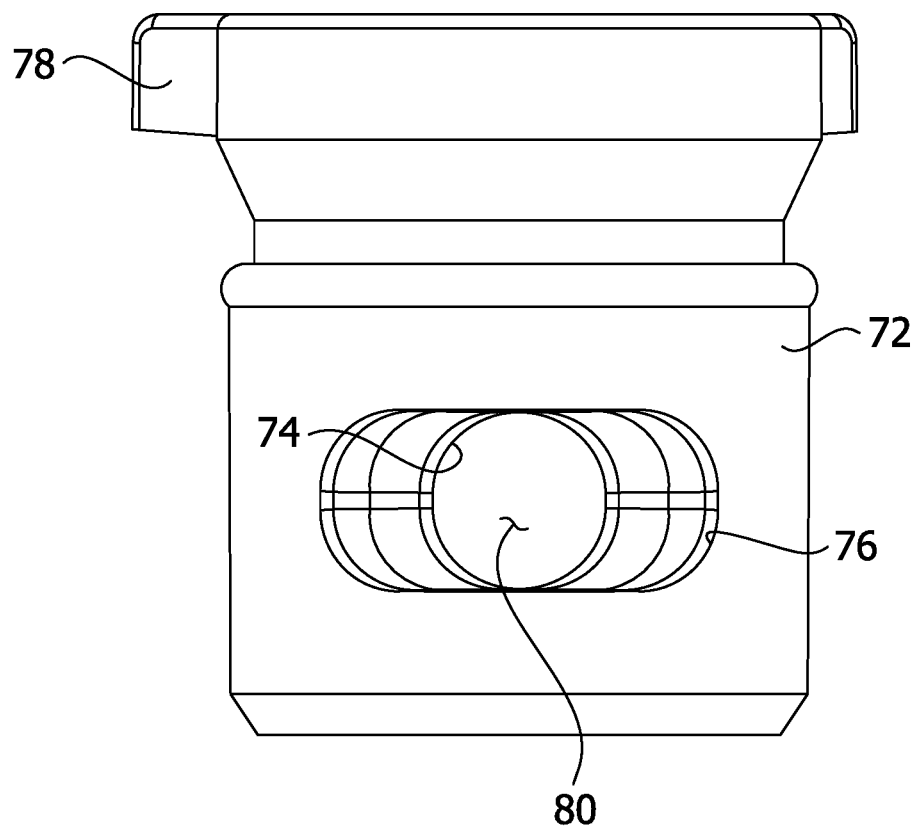
FIG. 11C is a side view of the stem.
Figure 12:
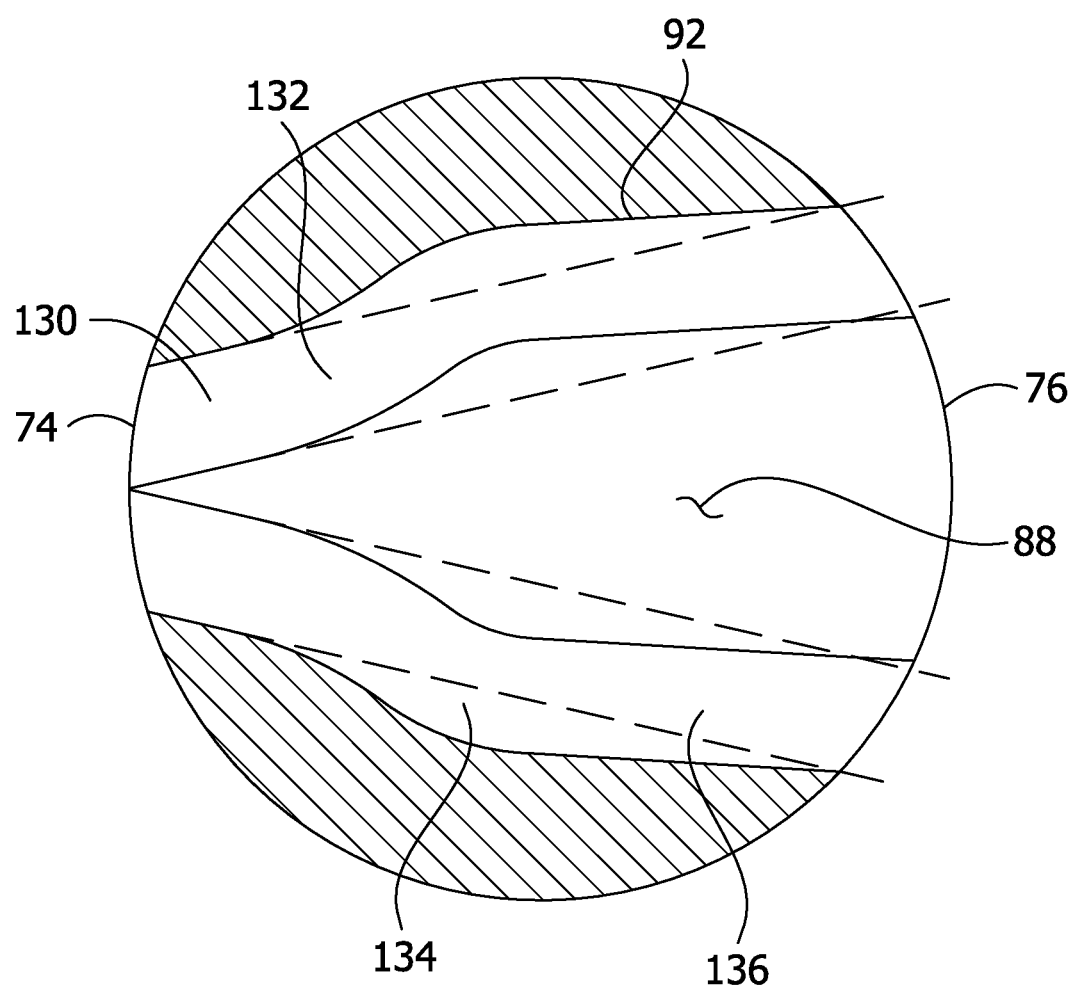
FIG. 12 is a cross section view of the stem.

As shown in FIG. 11B, flange 78 projects radially from the body 72 of the stem 68 and extends partially around a circumference of the body 72. In one embodiment, the flange 78 is generally fan-shaped. A cavity 80 is formed in the body 72 which allows a shaft 93 (FIG. 3) of the pump 1 to engage the body of the stem 68 for rotating the body in the opening 70. The flange 78 is configured to engage a hook 108 (FIGS. 2A and 3) in the recess 6 of the pump 1 to prevent removal of the feeding set 7 when the valve is open. The hook 108 is received in a recess 110 in the stem holder 66 (FIG. 10B) when the cassette 5 is attached to the pump 1. This locates the flange 78 adjacent to and behind at least a portion of the hook 108. As will be explained in greater detail below, movement of the stem 68 places the flange 78 behind the hook 108 preventing removal of the feeding set 7 when the valve is open. This safety feature prevents a free flow condition in the feeding set 7 where an uncontrolled amount of fluid is delivered to the patient which can be potentially harmful to the patient. Additionally, the flange 78 functions as a stop engagement feature for limiting rotation of the stem 68, as further explained below. The fitting 65 and stem 68 together may be considered a fitting assembly 82. The configuration of the fitting assembly 82 removes the fluid flow selection valve from the inlet tubing 77 and places it within the body of the cassette 5.

Figure 2A:
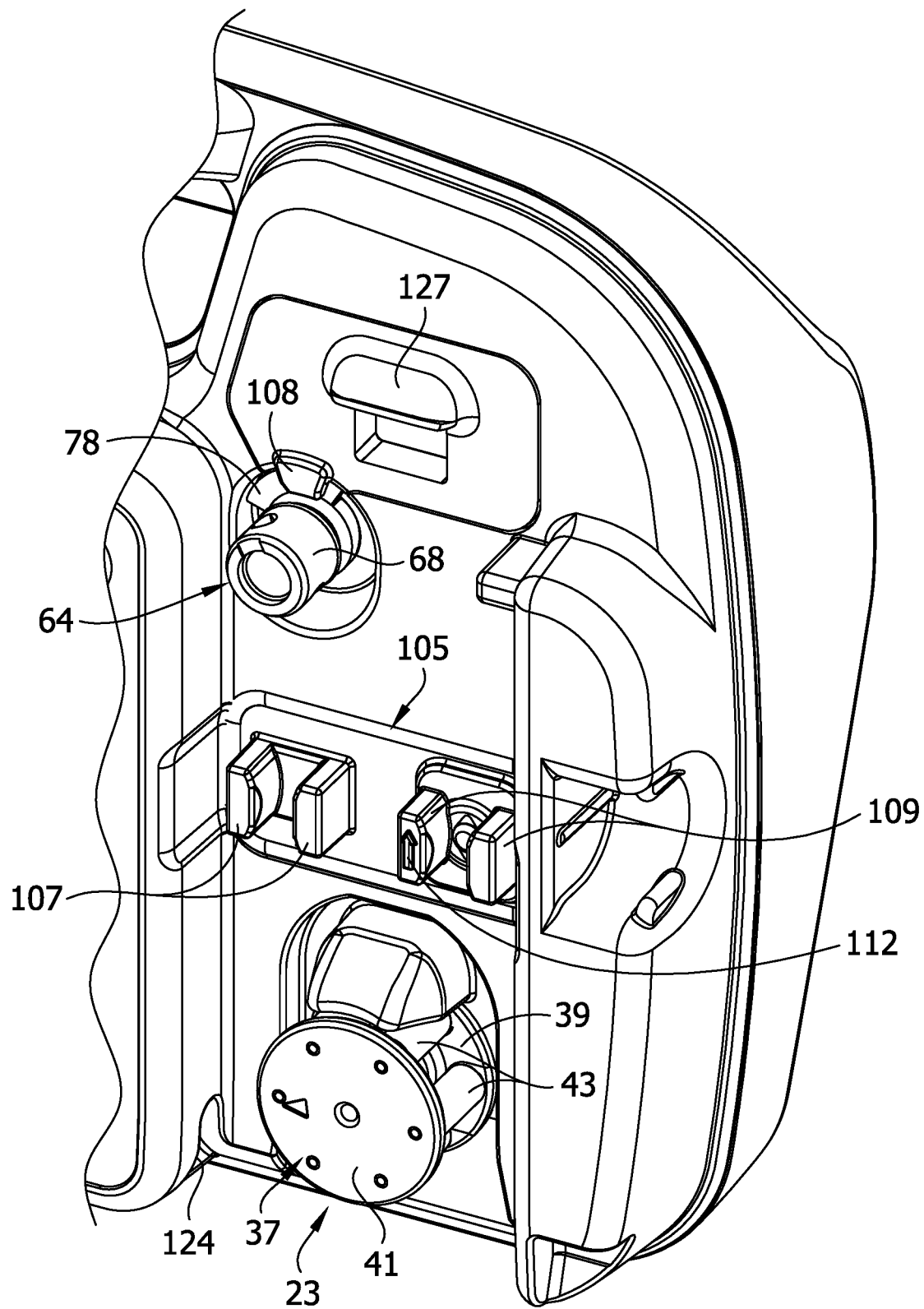
FIG. 2A is a fragmentary view of the perspective in FIG. 2 with the feeding set and portions of the cassette removed.
Figure 8:
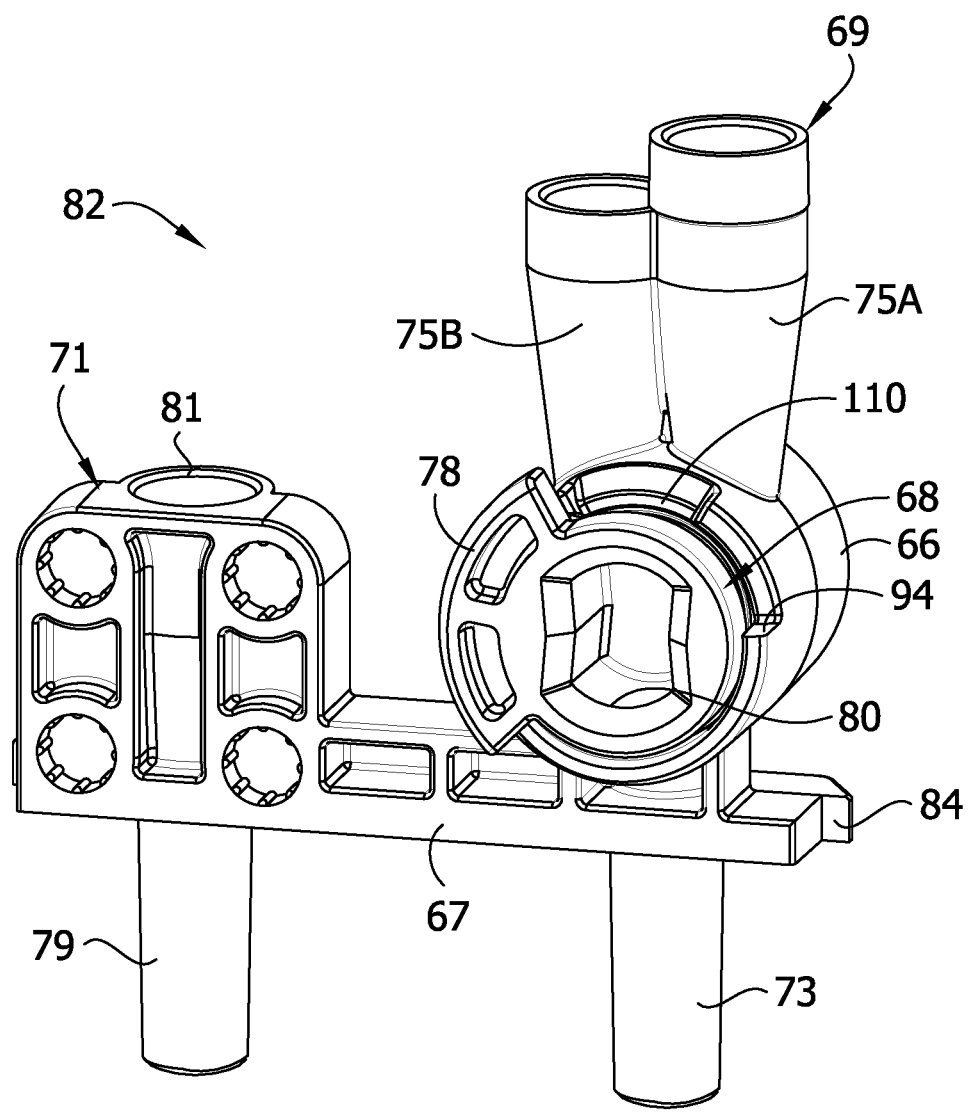
FIG. 8 is a front perspective view of the fitting assembly.
Figure 9:
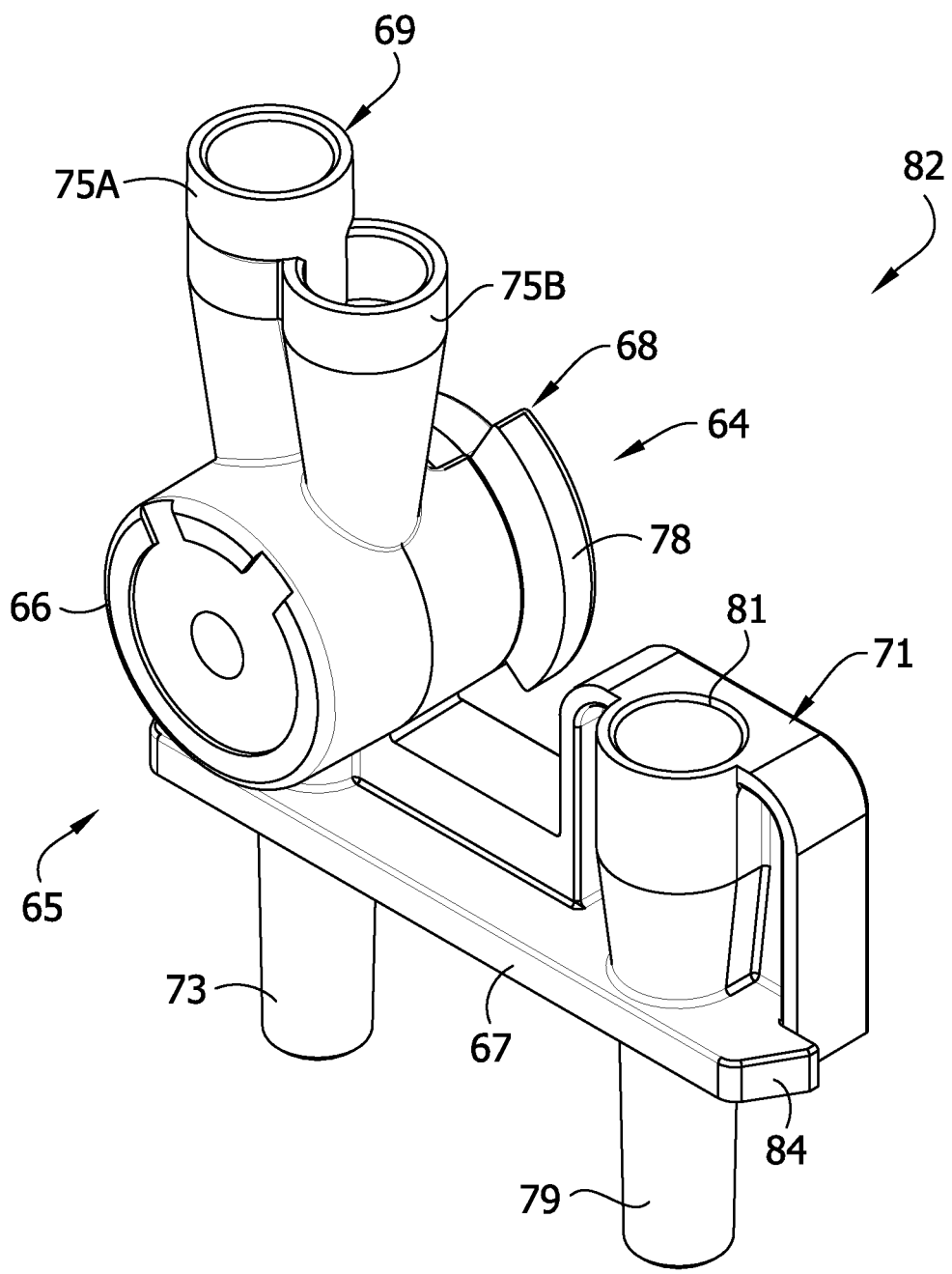
FIG. 9 is a rear perspective view of the fitting assembly.
Figure 10A:
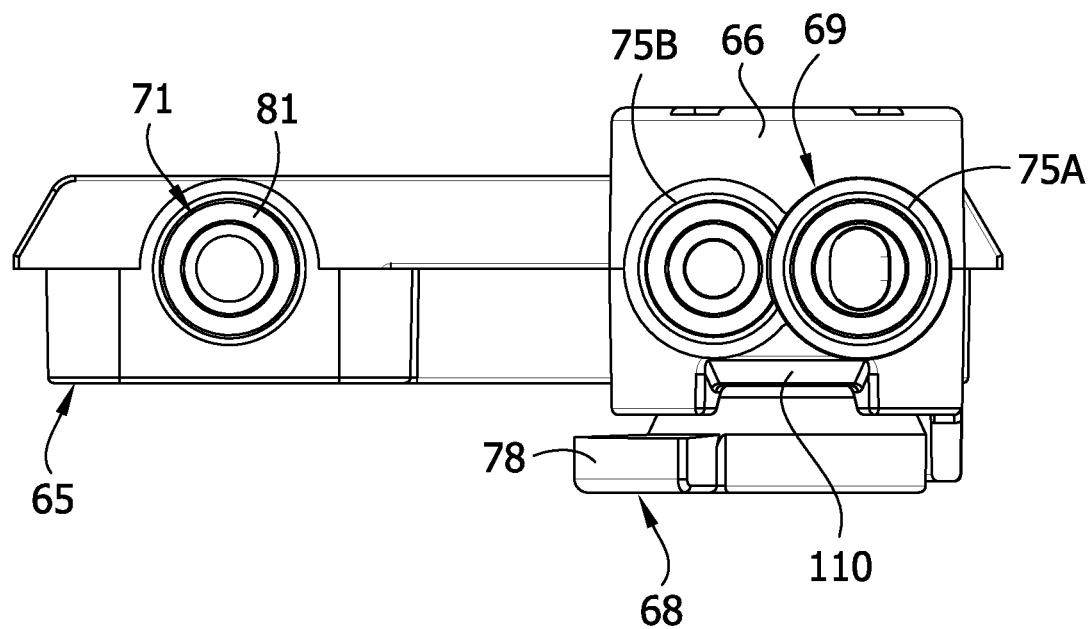
FIG. 10A is a top view of the fitting assembly.
Figure 10B:
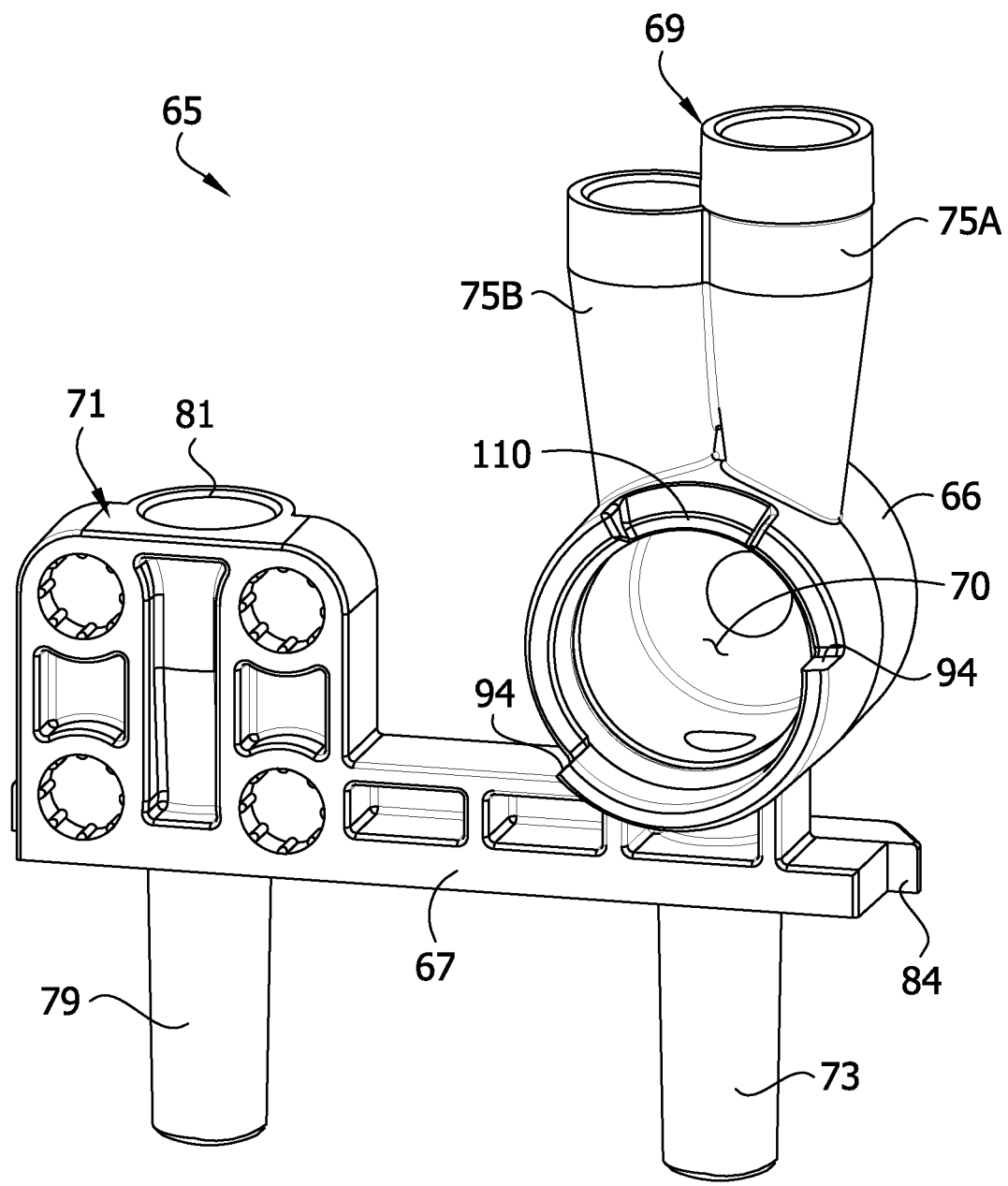
FIG. 10B is a front perspective view of the fitting assembly with a stem of a stopcock removed.
Figure 13A:
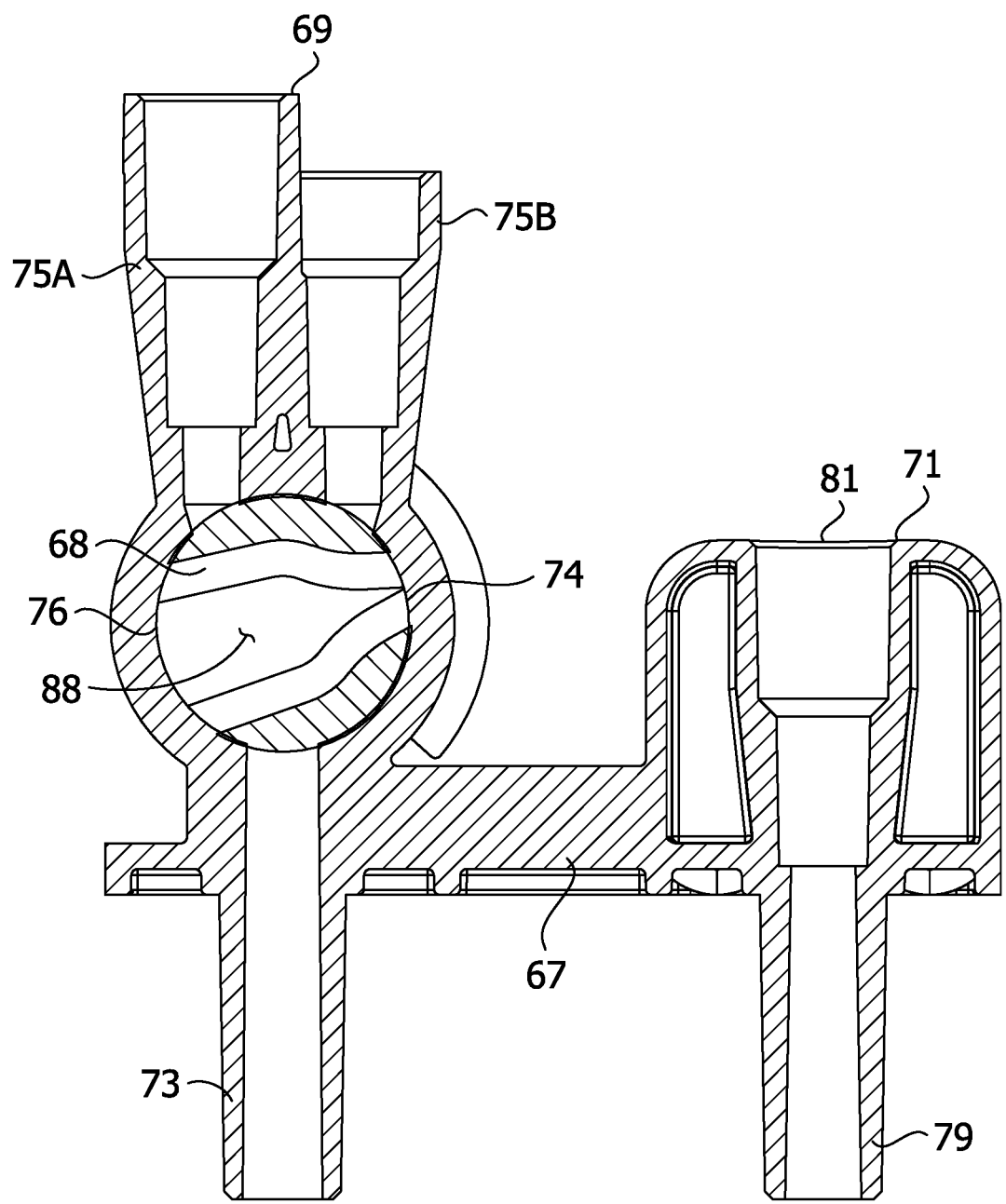
FIG. 13A is a vertical section view of the fitting assembly showing the stem in a fluid flow blocked position.
Figure 13B:
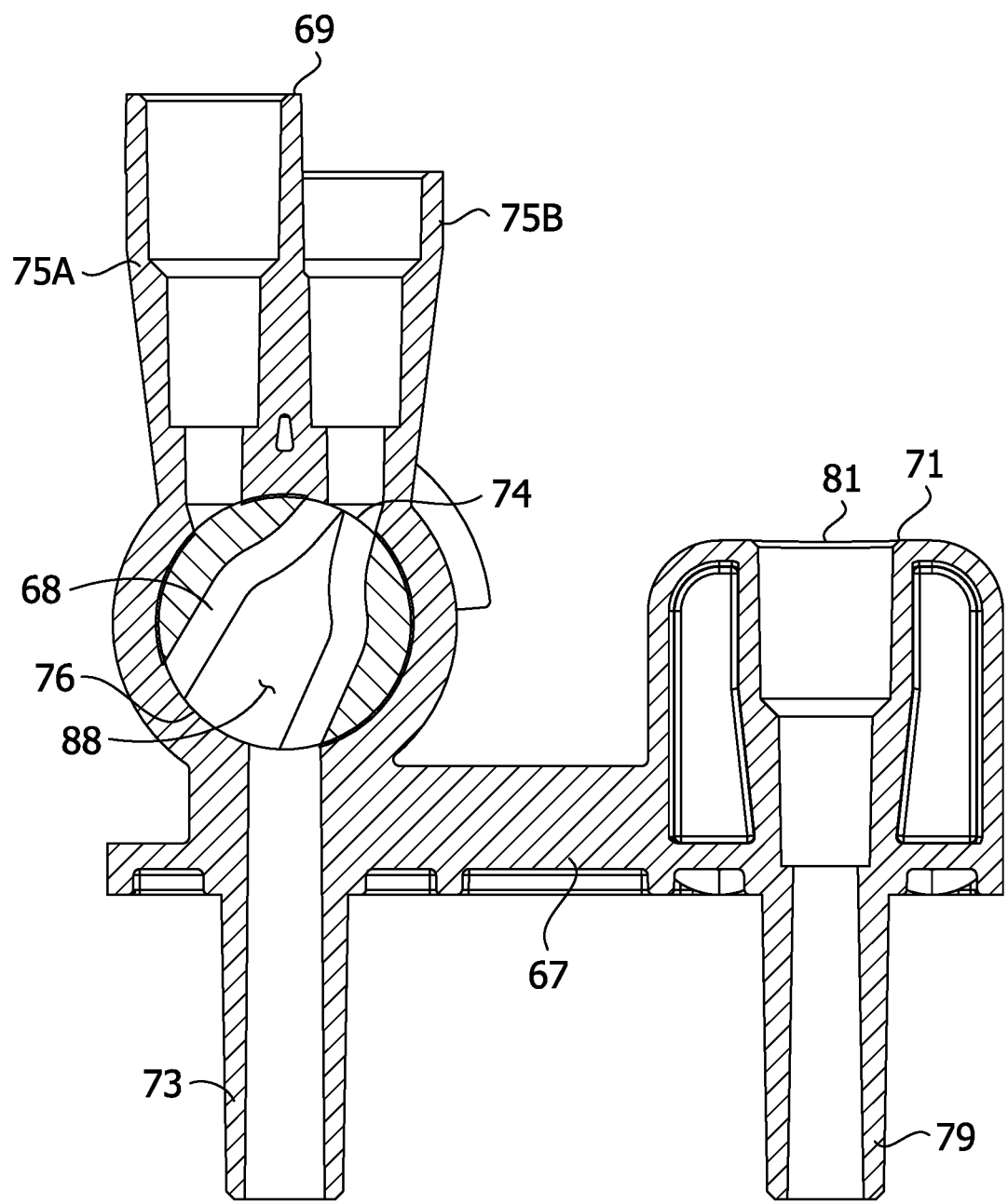
FIG. 13B is a vertical section view of the fitting assembly showing the stem in a flushing position.
Figure 13C:
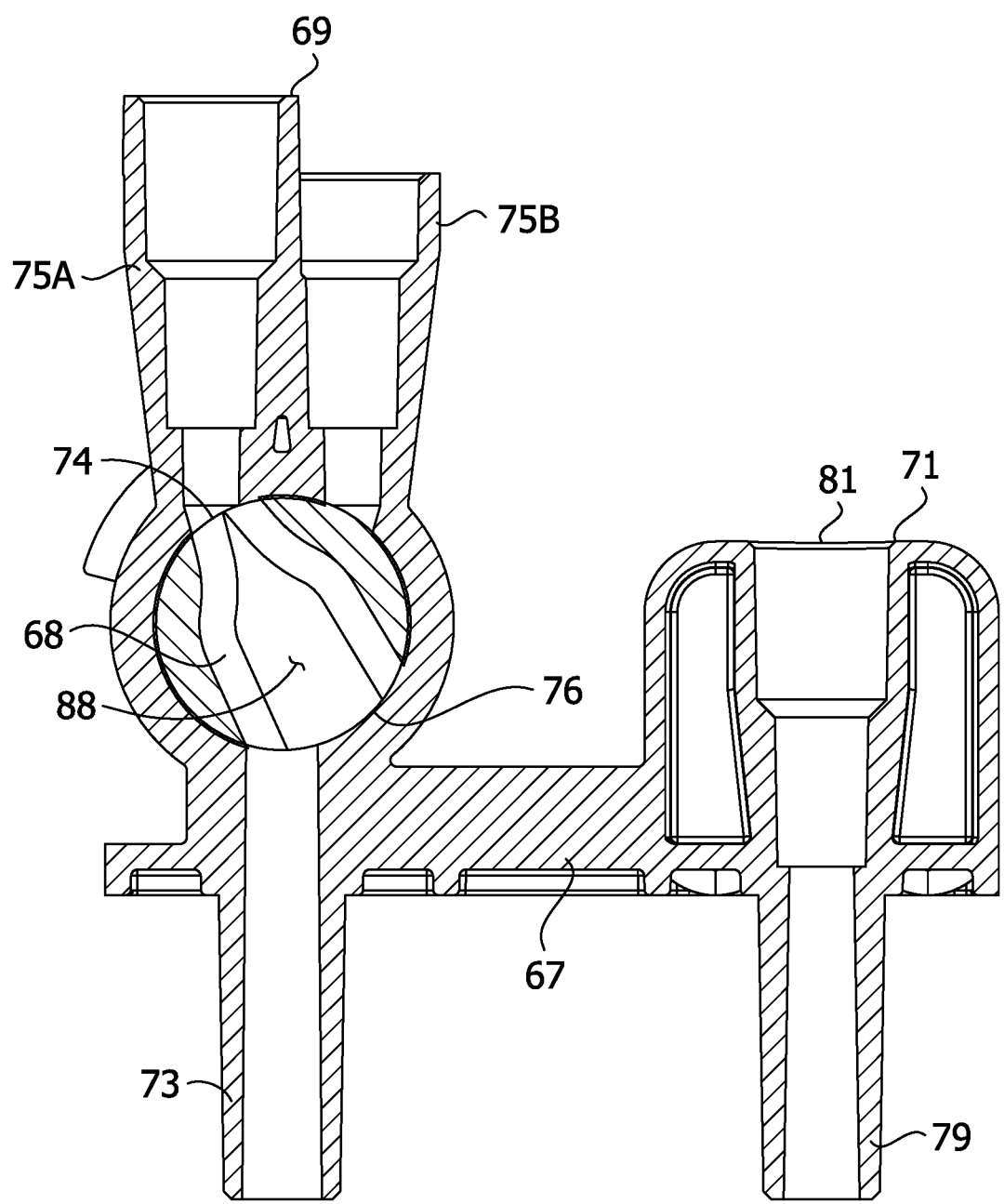
FIG. 13C is a vertical section view of the fitting assembly showing the stem in a fluid delivery position.
Figure 14:
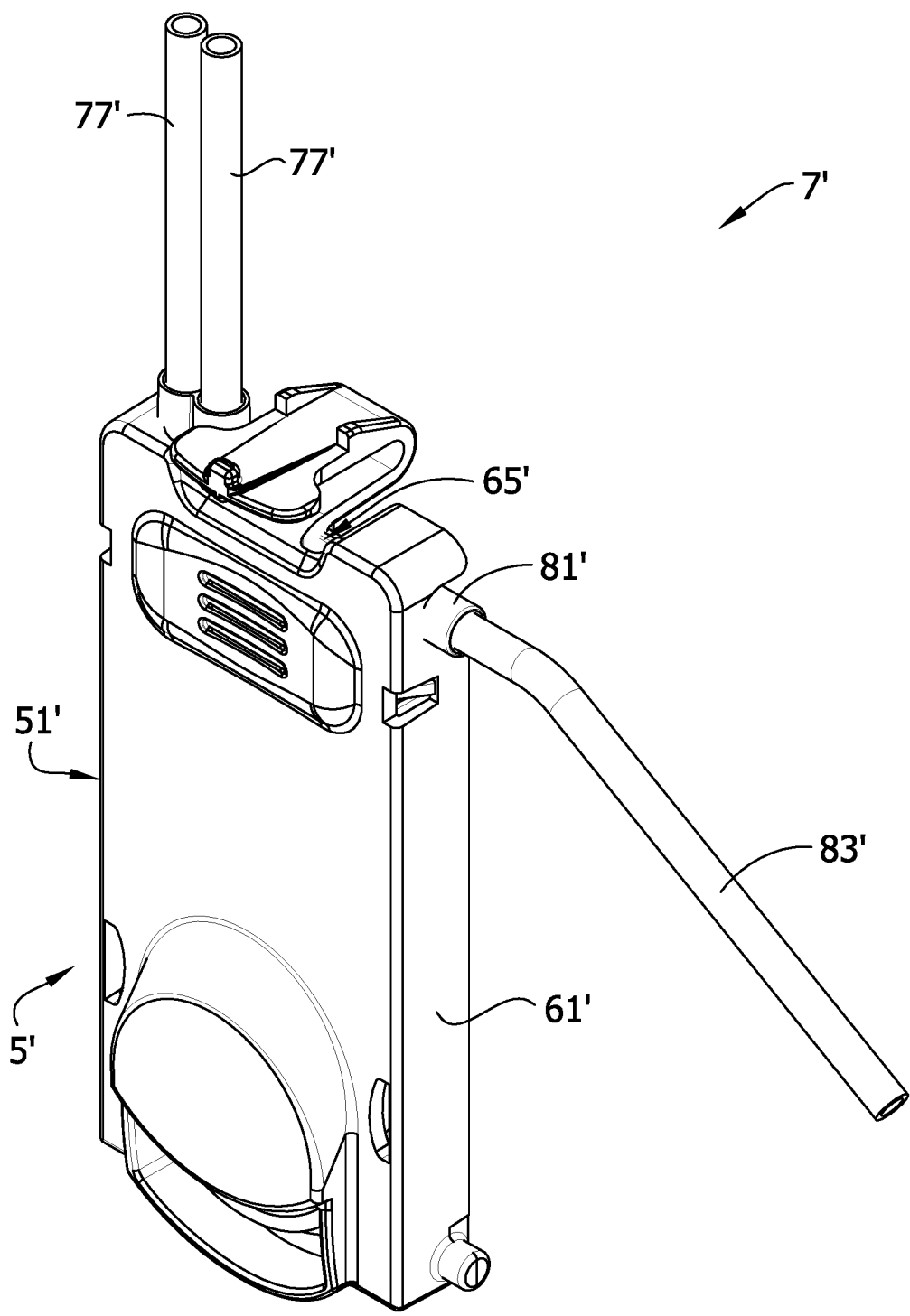
FIG. 14 is a perspective view of a cassette of another embodiment.
Figure 15:
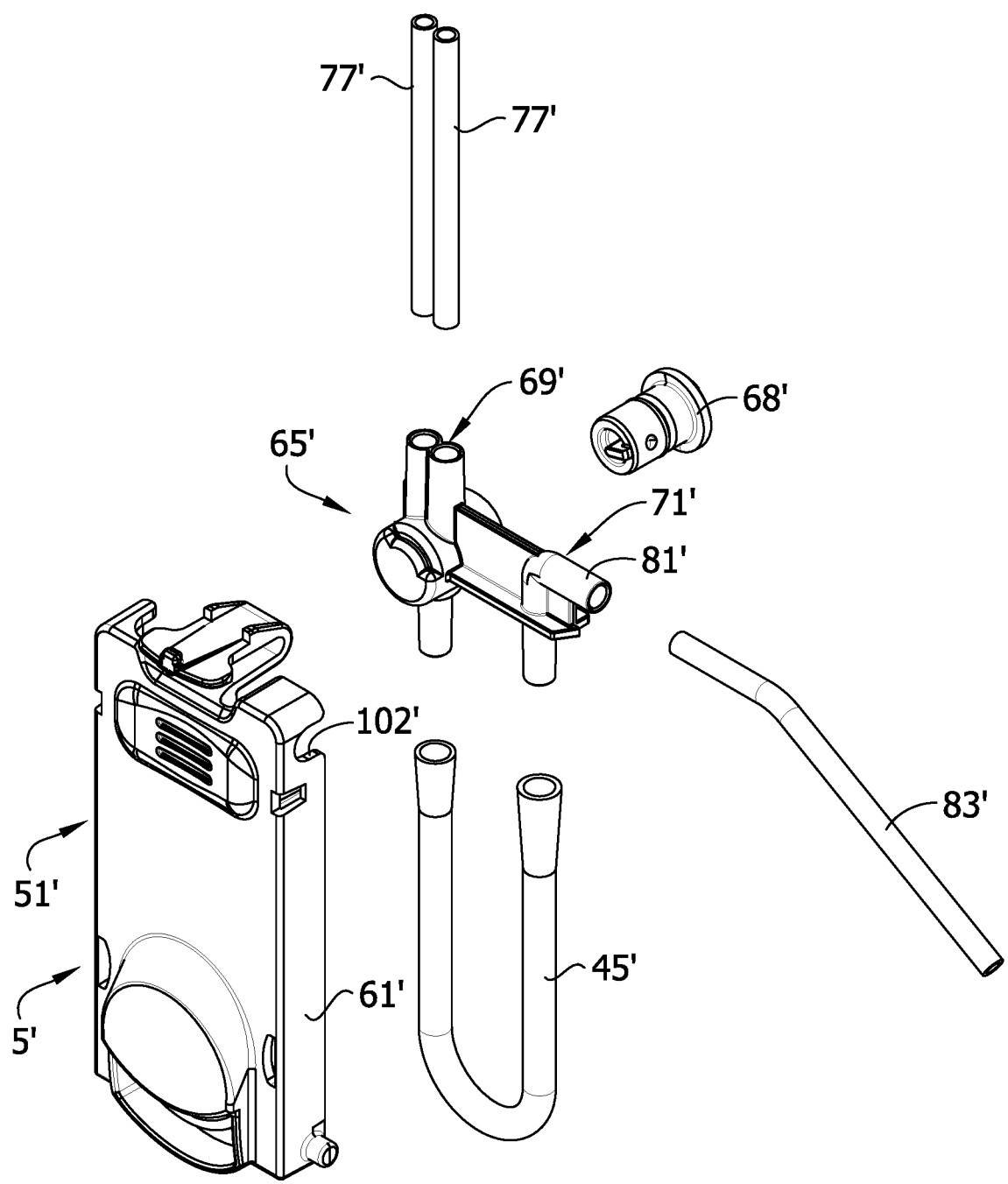
FIG. 15 is an exploded view of the cassette of FIG. 14.
Figure 16:
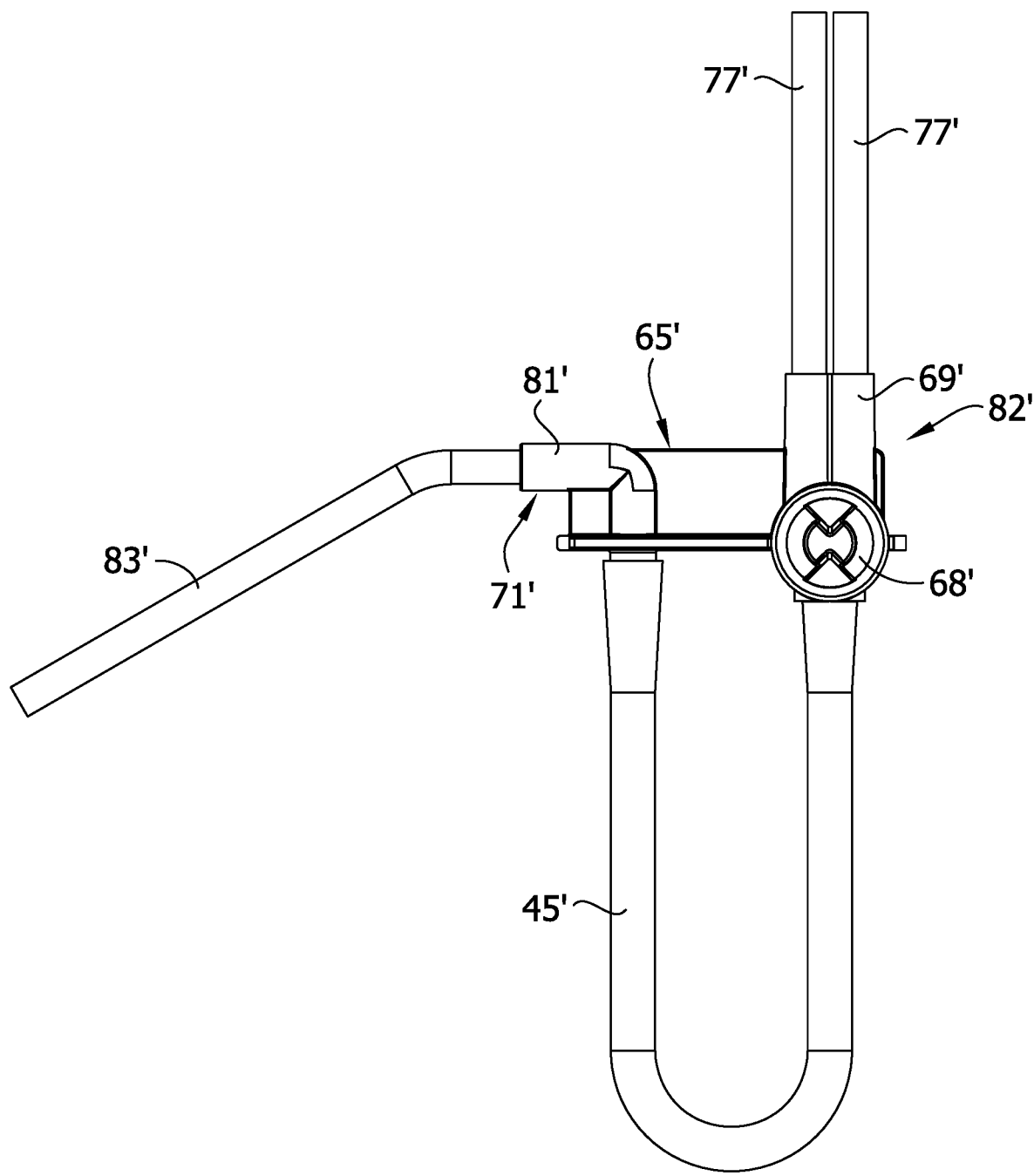
FIG. 16 is an elevation view of a portion of a feeding set of the cassette of FIG. 14.
Figure 17:
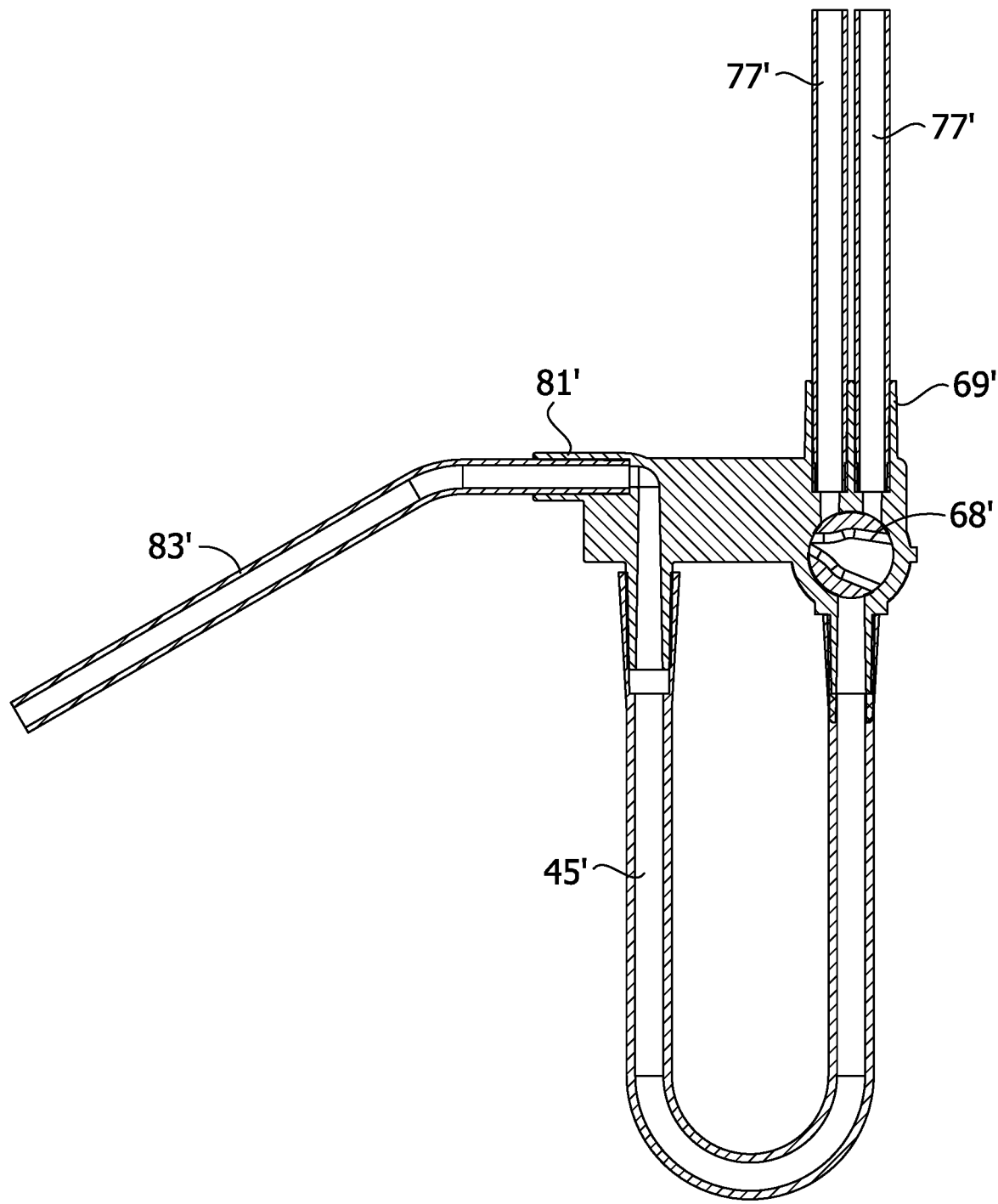
FIG. 17 is a vertical section view of the feeding set of FIG. 16.
Figure 18:
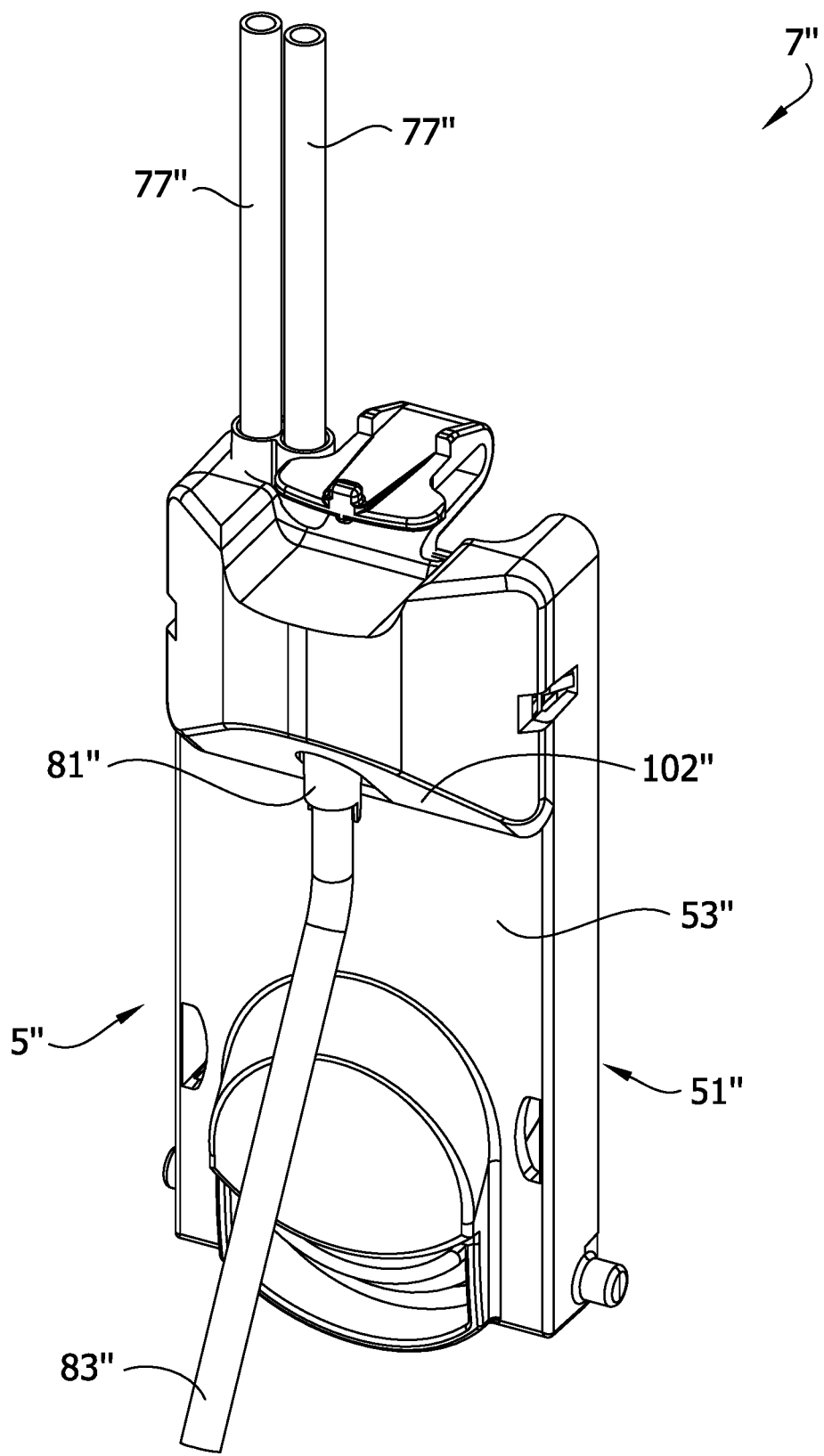
FIG. 18 is a perspective view of a cassette of another embodiment.
Figure 19:
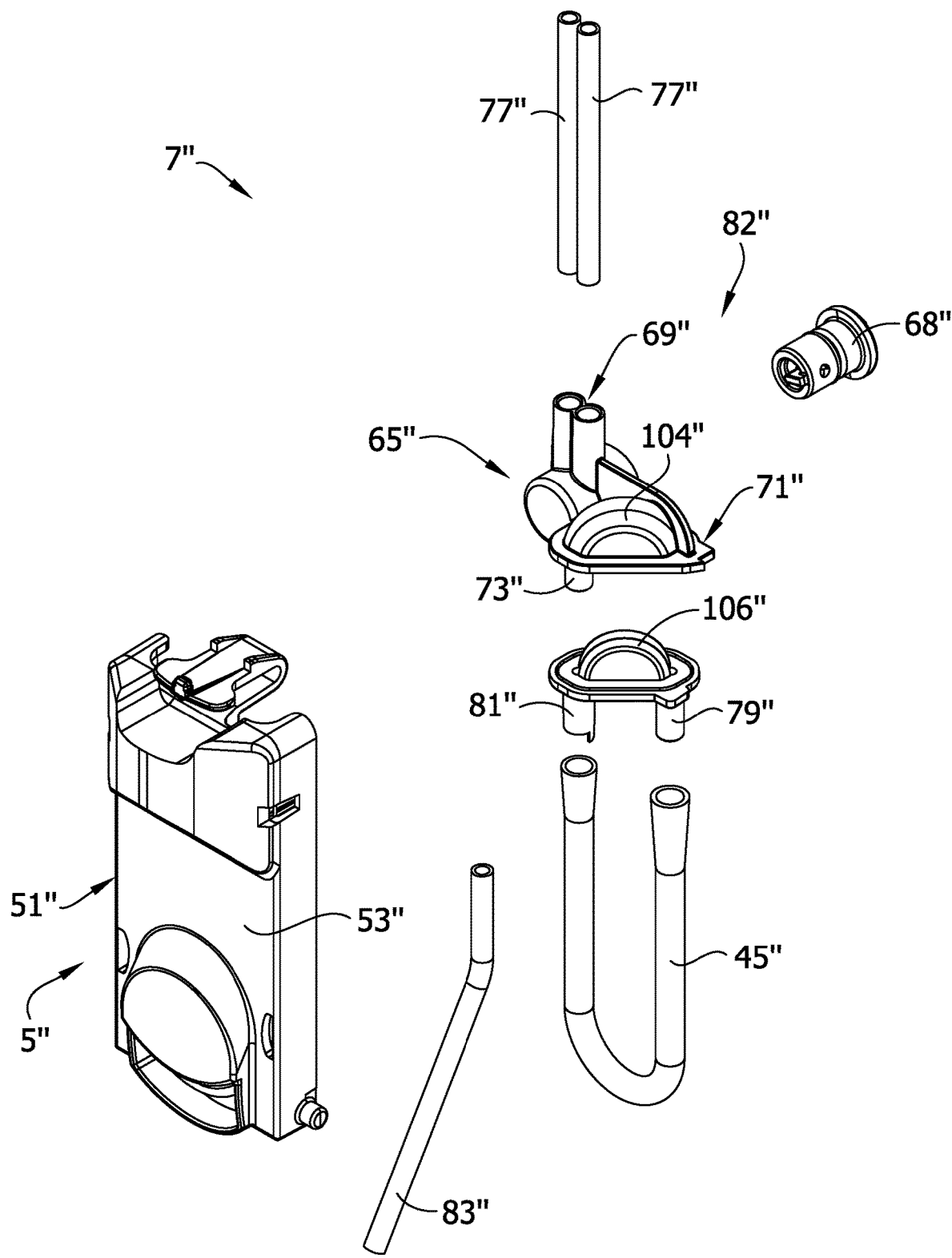
FIG. 19 is an exploded view of the cassette of FIG. 18.
Figure 20:
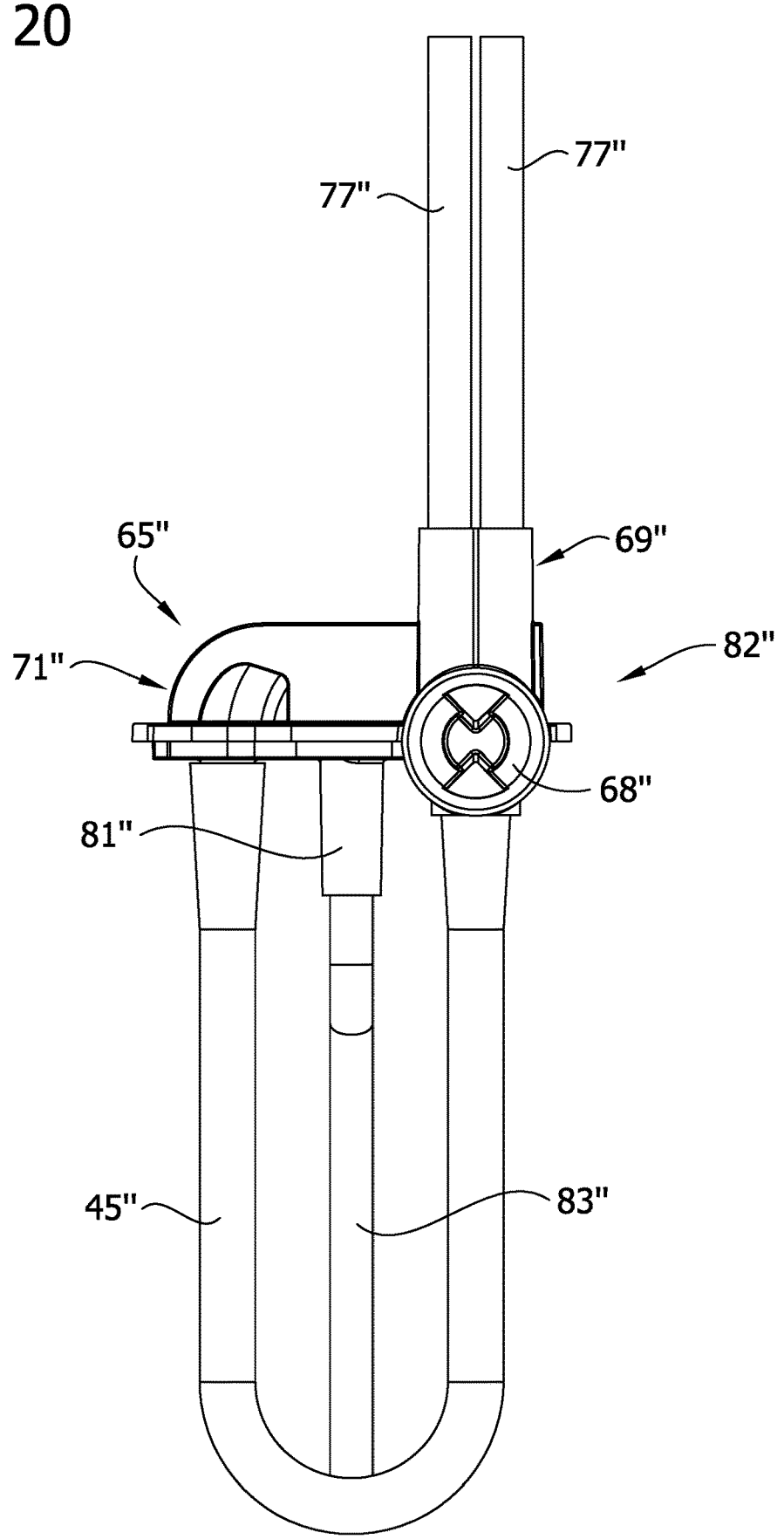
FIG. 20 is an elevation view of a portion of a feeding set of the cassette of FIG. 18.
Figure 21:
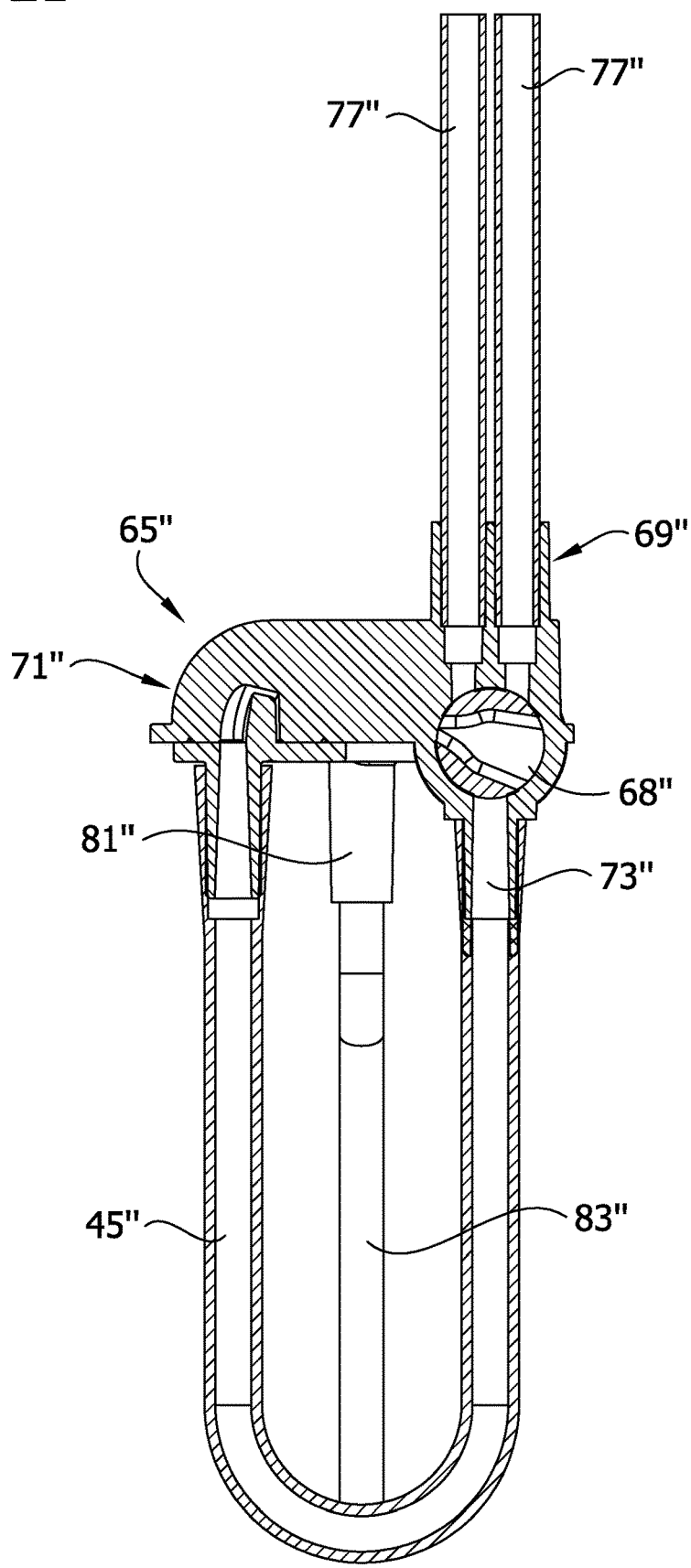
FIG. 21 is a vertical section view of the feeding set of FIG. 20.
Figure 22:
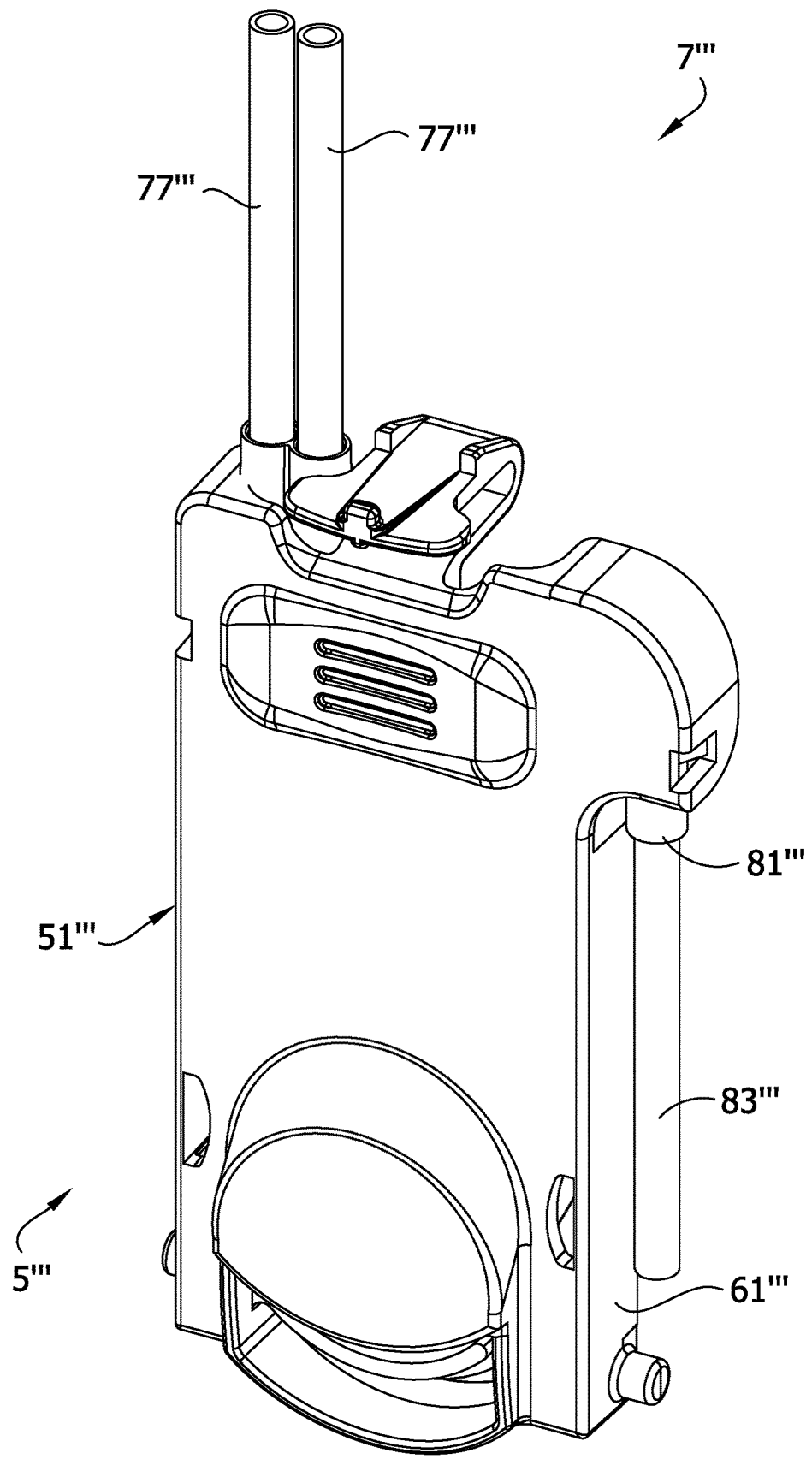
FIG. 22 is a perspective view of a cassette of another embodiment.
Figure 23:
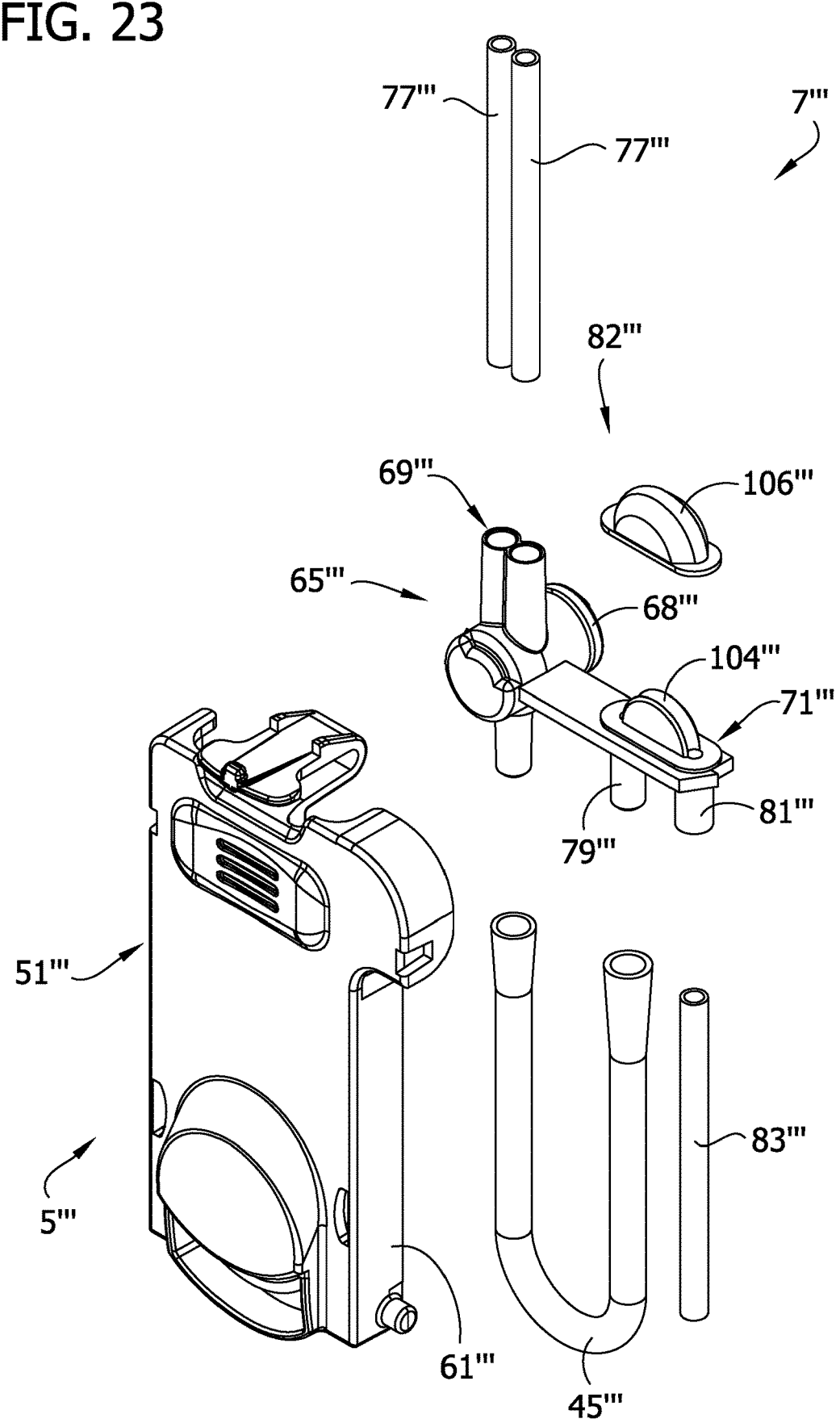
FIG. 23 is an exploded view of the cassette of FIG. 22.
Figure 24:
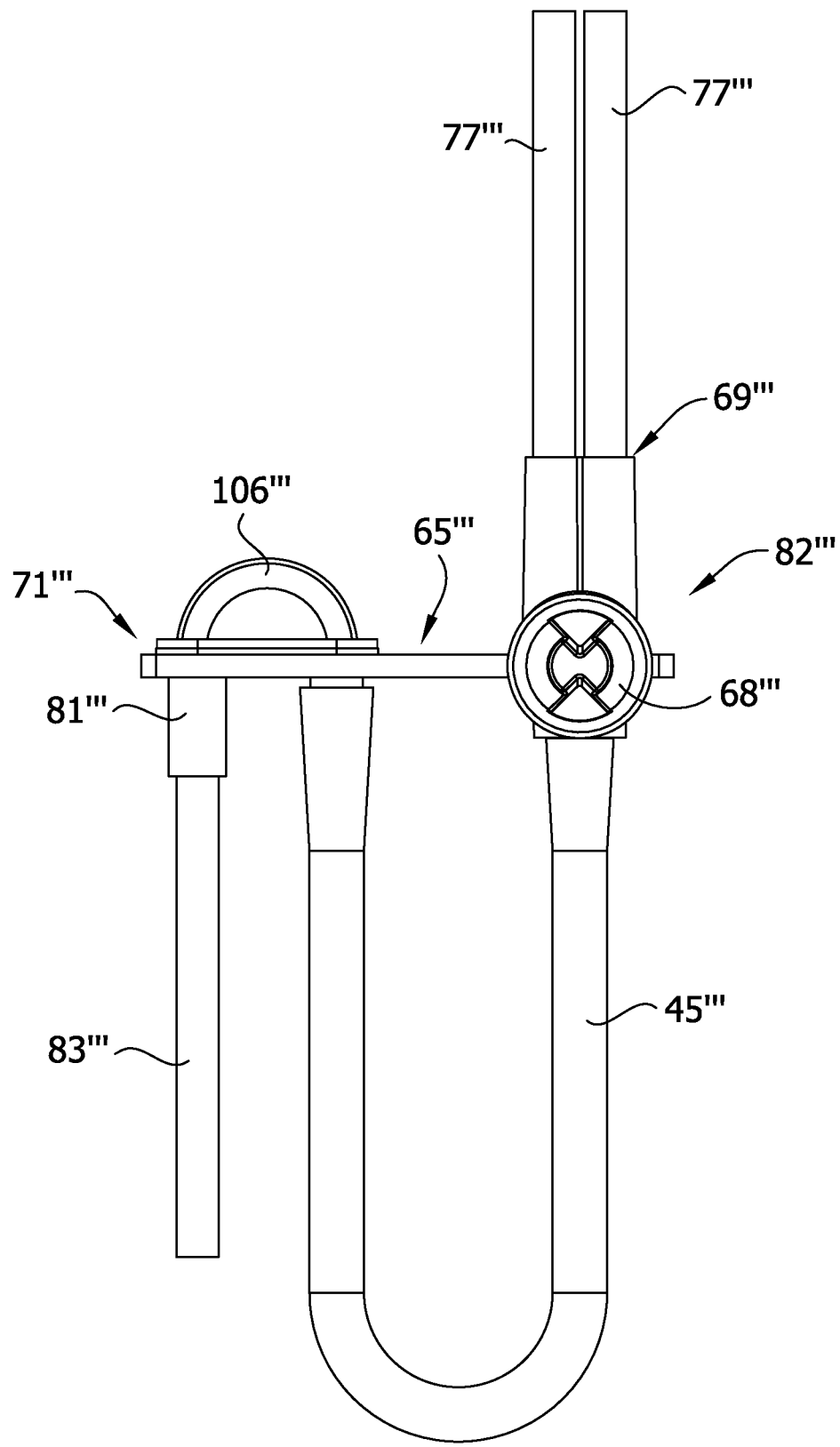
FIG. 24 is an elevation view of a portion of a feeding set of the cassette of FIG. 22.
Figure 25:
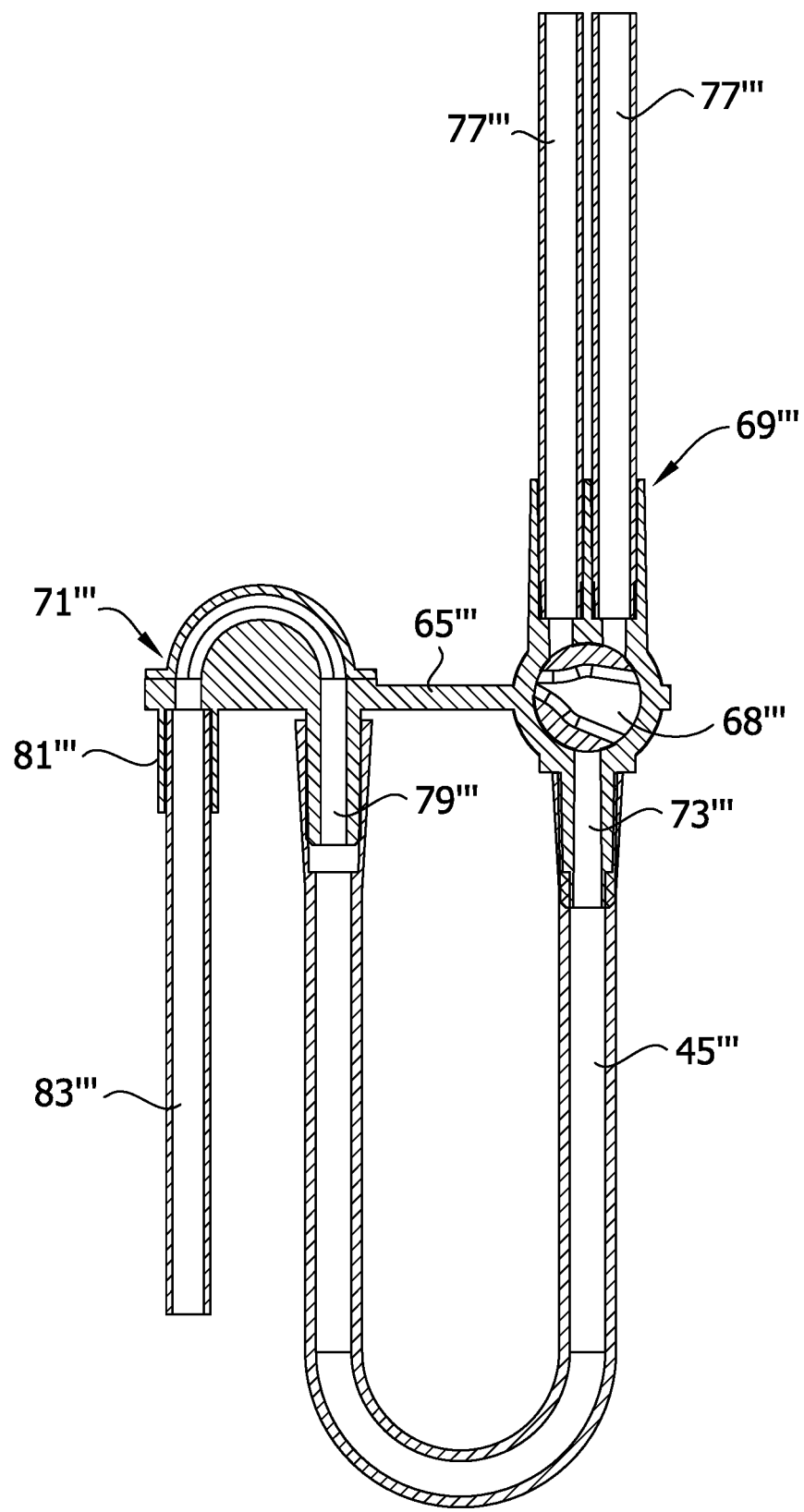
FIG. 25 is a vertical section view of the feeding set of FIG. 24.

In the configuration shown in FIGS. 8 and 13A, the fitting assembly 82 is in the fluid flow blocked configuration where the body 72 blocks the outlets of the second attachment portions 75A, 75B from communicating with the opening 70 and the inlet of the first attachment portion 73. Rotation of the stem 68, such as by the shaft 93 of the pump 1 engaging the cavity 80 and rotating the body 72 clockwise in the opening 70, will place the first opening 74 in communication with the outlet of second attachment portion 75B and the second opening 76 in communication with the inlet of first attachment portion 73 thereby placing the fluid source connected to second attachment portion 75B in fluid communication with the outlet 71 and outlet tubing 83 via tube 45 (FIG. 13B). The second attachment portion 75A remains blocked from communication with the first attachment portion 73. Additionally, when the stem 68 is rotated from a closed position to place the first opening 74 in communication with the outlet of second attachment portion 75B, the flange 78 moves behind the hook 108 on the pump 1 so that the feeding set 7 is prevented from being removed from the pump 1 (FIG. 2A). Further rotation of the stem 68 will place the first opening 74 in communication with the outlet of second attachment portion 75A and the second opening 76 will remain in communication with the inlet of the first attachment portion 73 thereby placing the fluid source connected to second attachment portion 75A in communication with the outlet 71 and outlet tubing 83 via tube 45 (FIG. 13C). This is accomplished because the position and length of the second opening 76 are such that at least some portion of the second opening will be in communication with the inlet of the first attachment portion 73 throughout the movement of the stem 68 to communicate the first opening 74 with the outlets of the second attachment portions 75A, 75B. The second attachment portion 75B is now blocked from communication with the first attachment portion 73. Stops 94 on the stem holder 66 engage the flange 78 to limit rotation of the body in the opening 70.

Figure 5:
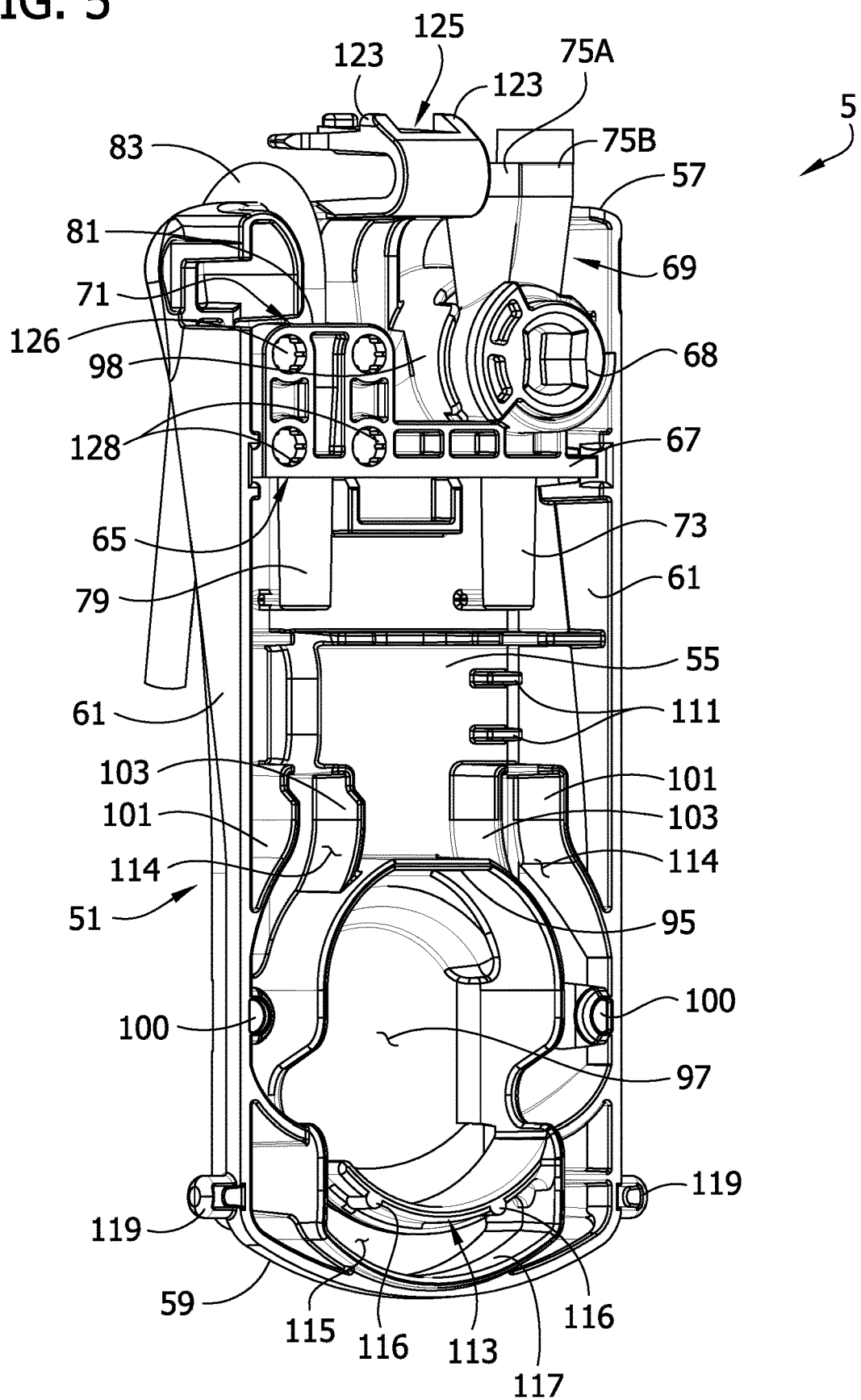
FIG. 5 is a rear perspective view of the cassette.
Figure 6:
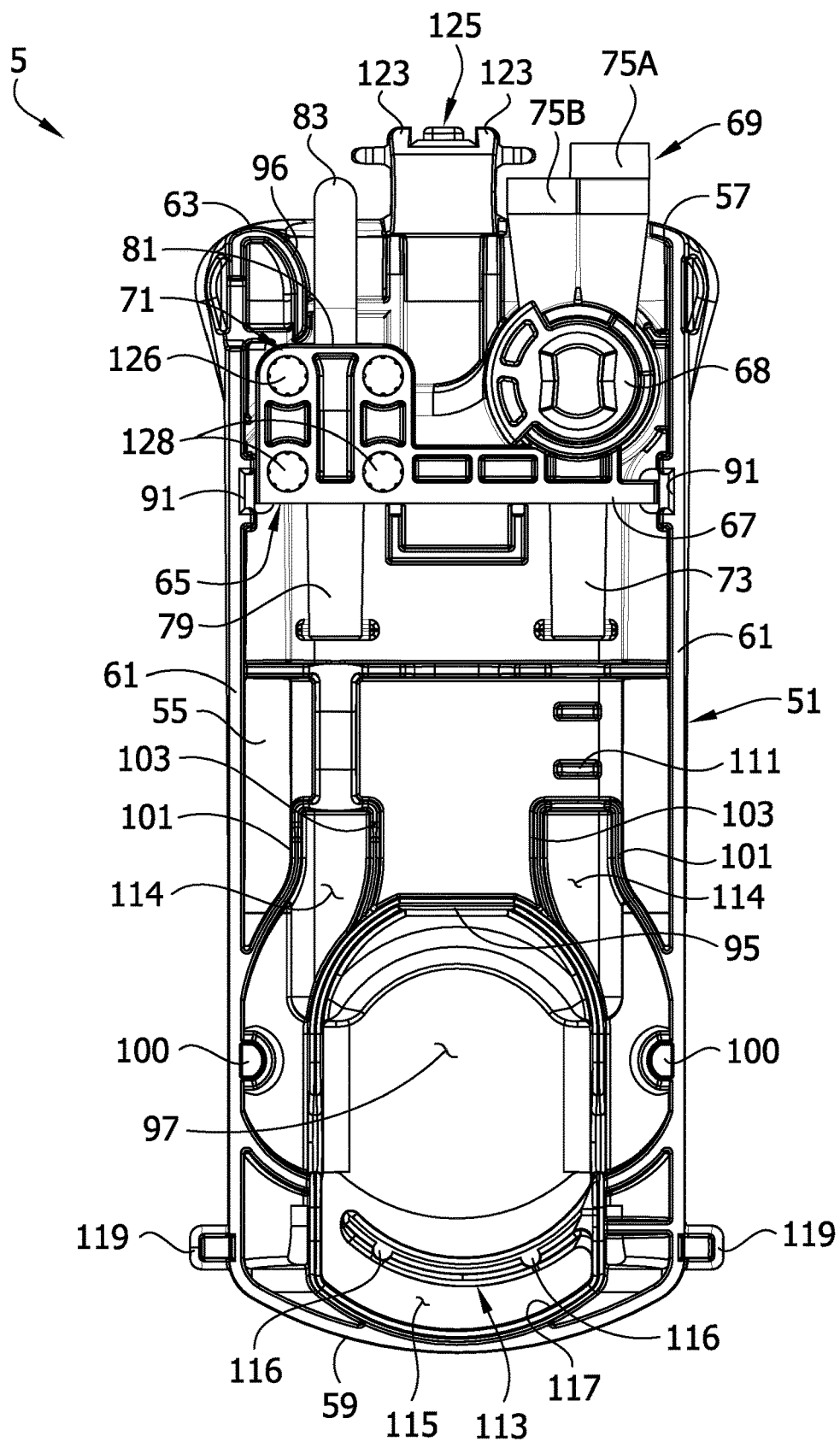
FIG. 6 is a rear elevation view of the cassette.
Figure 7:
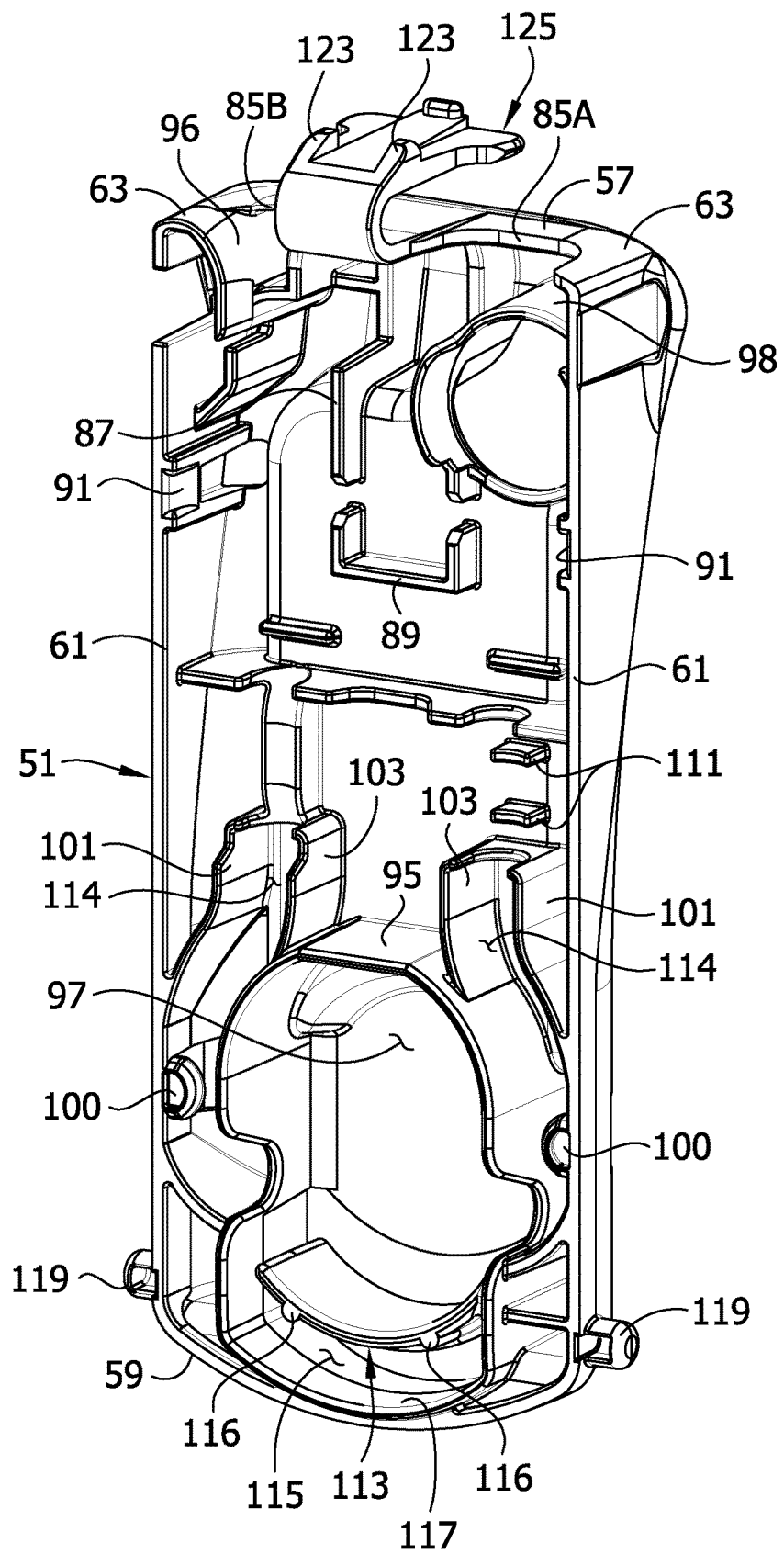
FIG. 7 is the rear perspective view of the cassette with a fitting assembly removed from the cassette.

Referring to FIGS. 5-7, the second attachment portion 81 of the outlet 71 of the fitting 65 is recessed from the top 57 of the cassette 5 so that the outlet tubing 83 extends down into the body 51 of the cassette prior to being inserted into the second attachment portion 81. This provides a section of the outlet tubing 83 that extends adjacent a curved guide wall 96 extending down from the top wall 63. The curved guide wall 96 provides an arcuate surface of gradually decreasing slope for the outlet tubing 83 to rest on preventing the tubing from bending sharply on a transverse edge of the cassette 5. As a result, the outlet tubing 83 is prevented from kinking, which can inhibit fluid flow through the tubing. Additionally, because a section of the outlet tubing 83 extends between the top 57 of the cassette 5 and the attachment of the tubing to the fitting 65, the section of the tubing inserted into the second attachment portion 81 which may have been softened by the treatment of the solvent is not located where the tubing is subject to a bending force. Rather, this section is spaced away from the top 57 of the cassette 5 and is held generally straight by the curved guide wall 96. This further reduces the chances of any kinking or pinching off in the outlet tubing 83.

As exemplarily illustrated, tabs 84 (FIGS. 8 and 9) can extend from lateral sides of the base 67 and can be configured to be received in respective openings 86 (e.g., FIGS. 1 and 4) in the front 53 of the cassette 5 to releasably attach the fitting 65 to the cassette 5. A pair of guide ramps 91 (FIGS. 6 and 7) in the side walls 61 may funnel toward the openings 86. The tabs 84 on the fitting 65 can ride along the ramps 91 and be received in the openings 86 to retain the fitting to the cassette body 51. The stem holder 66 of the fitting 65 is received in a valve holder 98 (FIG. 7) formed in the body 51 of the cassette 5. Alternatively, the fitting 65 may be formed integrally with the cassette body 51, or omitted.

Referring to FIGS. 5 and 7, cutouts 85A, 85B may be formed in the top wall 63 of the cassette body 51 for receiving the second attachment portions 75A, 75B of the inlet 69 of the fitting 65, and the outlet tubing 83, respectively. A locator wall 87 may extend vertically near the top of the cassette body 51. A generally U-shaped wall 89 may be disposed between the side walls 61 generally at a center of the cassette body 51. The base 67 of the fitting 65 is received between the locator wall 87, and the U-shaped wall 89. The base 67 may engage a bottom of the locator wall 87 and tops of vertical projections of the U-shaped wall 89 to position the fitting 65 in the cassette 5.

Figure 4:
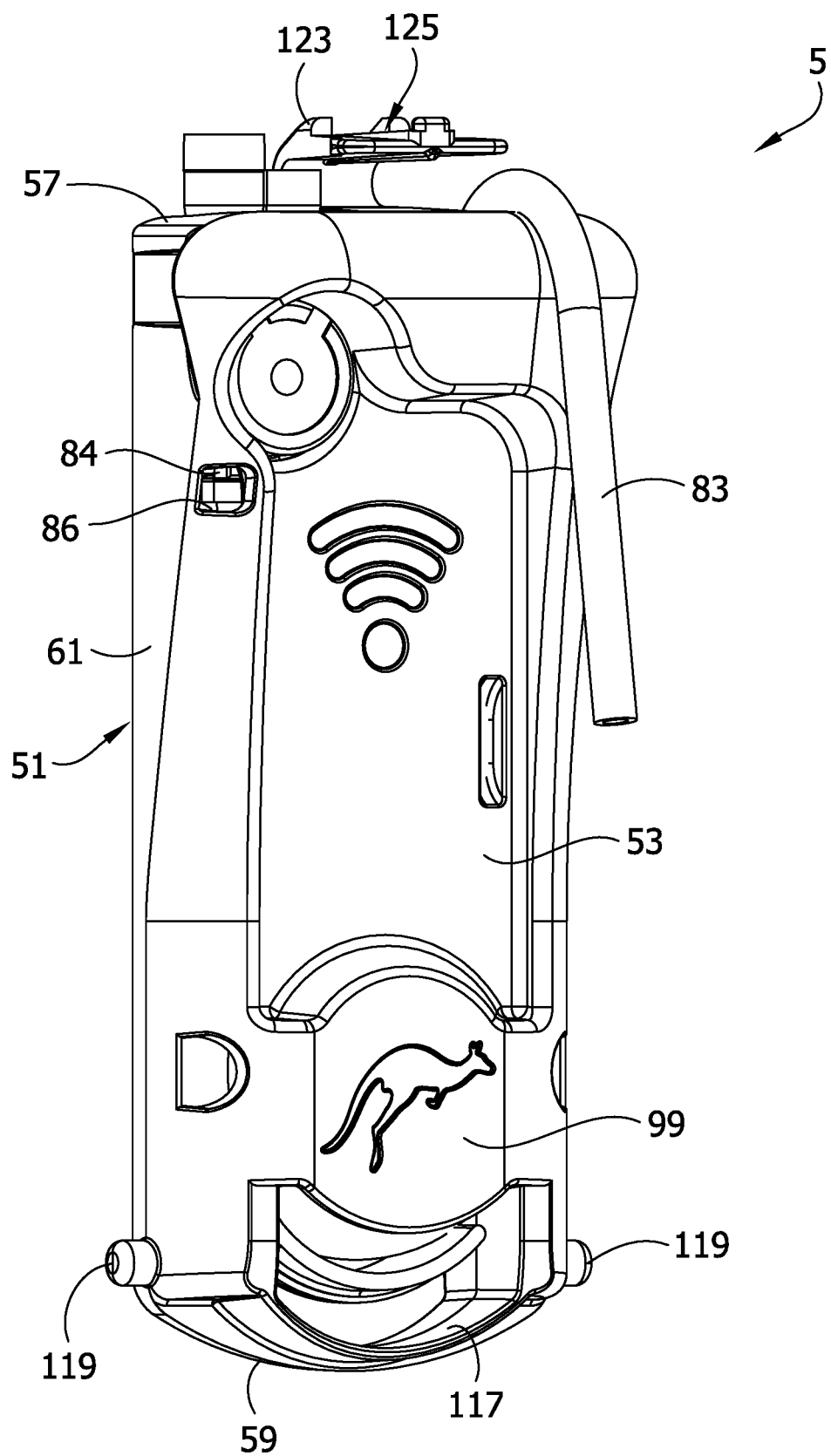
FIG. 4 is front perspective view of the cassette.

An arcuate wall 95 may be disposed generally at a middle of the cassette body 51 to at least partially define a rotor recess 97 for receiving at least a portion of the rotor 37 of the pump 1 when the cassette 5 is attached to the housing 3. The rotor recess 97 may include a bump-out 99 on the front 53 of the cassette body 51 (FIG. 4). Inlet and outlet outer curved guide walls 101 may extend generally parallel to opposite sides of arcuate wall 95. Inlet and outlet inner curved guide walls 103 may extend upward from the arcuate wall 95 generally parallel to the inlet and outlet outer curved guide walls 101, respectively, forming inlet and outlet openings for receiving and supporting respective inlet and outlet portions of the tube 45. The guide walls 101, 103 and arcuate wall 95 may form a tube channel 114 for receiving a lower portion of the tube 45 in a looped configuration to properly position the tube relative to the rotor 37 when the cassette 5 is attached to the housing 3. The arcuate wall 95 and curved guide walls 101, 103 may receive the tube in close fitting relation around the sides of the rotor recess 97. Tabs 100 may extend over the tube channel 114 to hold the tube 45 in the tube channel 114 and to retain the tube 45 in the cassette, constraining the tube according to a third axis. The outer curved guide walls 101 may terminate generally at a bottom side of the rotor recess 97 so that the tube 45 is not directly opposed by the guide walls 101, 103 or the arcuate wall 95 at the bottom of the rotor recess 97.

An insert 105 may be received in the cassette recess 6 in the housing 3 to aid in securing the cassette 5 and tube 45 in the cassette recess 6 (FIG. 3). The insert 105 may be positioned in the recess 6 such that the insert 105 is received in the back cavity of the cassette 5 above the curved guide walls 101, 103 when the cassette 5 is attached to the housing 3. The insert 105 may comprise a pair of opposing first projections 107 disposed at an inlet side of the insert for receiving the inlet portion of the tube 45, and a pair of opposing second projections 109 disposed at an outlet side of the insert for receiving the outlet portion of the tube. Ribs 111 (FIGS. 6 and 7) on the back 55 of the cassette body 51 may be positioned to engage the outlet portion of the tube 45 between the second projections 109 to aid in inserting the outlet portion between the projections. Indicia 112 may be disposed on at least one of the second projections 109 indicating the direction of fluid flow in the tube 45. In the illustrated embodiment, the indicia 112 is in the form of an arrow.

Referring to FIGS. 5-9, a stator member 113 may be disposed a bottom portion of the cassette body 51 in a cavity such as stator opening 115 generally at or proximate the bottom of the rotor recess 97. Thus, when the cassette 5 is attached to the housing 3, the stator member 113 is typically positioned generally opposite a bottom of the rotor 37. In advantageous configurations, the stator member 113 may support the tube 45 of the feeding set 7 when the rollers 43 engage the tube, as explained below. In some cases, the stator member 113 may have an arcuate shape extending along a length of the stator member. As in the exemplarily illustrated embodiments, the stator member 113 may be a cantilevered member anchored only at a first end to the cassette body 51 and at least partially free to float in the stator opening 115 relative to the cassette body 51. As shown, the flexible stator member 113 may pivot about its connection or anchor to the remainder of the cassette 5 and may partially or fully flatten out upon engagement with a roller 43. For example, the stator member can have the first end affixed to the cassette body and a second end that is unfixed which can float or be displaced to allow a reaction segment having a surface of the stator member to have a deflection displacement. For example, as the at least one roller traverses along the tube while revolving about the axis of rotation of the rotor, the flexible stator member 113 may be displaced or deflect to a deflection displacement in reaction to the applied force by the one or more rollers 43 during revolution thereof about the axis of rotation.

Transverse ribs 116 on a bottom of the first section can provide structural rigidity to the flexible stator member 113 and can serve as contacting surfaces that facilitate removal, such as by ejection, of the flexible stator member from a mold cavity. In the illustrated embodiment, the flexible stator member 113 may be integrally formed as one piece with the cassette body 51. However, the flexible stator member 113 could be formed separately from the cassette body 51 and attached to the cassette body by a suitable means. For example, a flexible stator (not shown) can have an elongate extension portion that is engaged in an engagement cavity in the cassette body wherein the engagement cavity is correspondingly sized and shaped to receive the extension portion. In this manner, a stator member can be selected from a plurality of candidates of differing mechanical characteristics, such as modulus and radius of curvature, to tailor the cassette operating parameters, with or without consideration for any of the tube characteristics, and provide specific flow performance attributes during pumping operation.

A stop 117 may be disposed at a bottom of the stator opening 115 to limit the floating movement of the flexible stator member 113 to a maximum displacement. The stop 117 may be spaced relative to the underside of the flexible stator member 113 to prevent flexing of the stator member that would result in plastic deformation of the stator member. For example, the stop member may be positioned to limit the magnitude of the deflection displacement distance of the unfixed end to the maximum displacement. In the illustrated embodiment, the stop 117 is formed as part of the cassette body 51. However, the stop 117 could be formed separately from the cassette body 51 and attached to the cassette body in a suitable fashion. In other cases, stop 117 may be formed on the housing 3 and configured to limit the displacement of the flexible stator member 113 to the maximum displacement. The stop 117 may have a width that is greater than the width of the flexible stator member 113 so that the stop provides an adequate surface area to limit movement of the stator member. The stop 117 can serve to shield the flexible stator member 113 and is typically sized to prevent or reduce the likelihood of snagging or catching the member 113.

Prior to attaching the cassette 5 to the pump housing 3, the inlet and outlet tubing 77, 83 may be attached to the inlet and outlet 69, 71, respectively, of the cassette. To attach the cassette 5 to the pump housing 3, one or more pins or raised projections 119 at the bottom 59 of the cassette body 51 may be inserted in slots 124 at the bottom of the recess 6 in the housing 3. The engagement between the raised projections 119 and slots 124 generally locates the cassette 5 on the housing 3. The cassette body 51 can then be rotated up until ledges 123 on a tab 125 at the top 57 of the cassette body are captured by a catch 127 at the top of the recess 6. In the illustrated embodiment, the raised projections 119 and ledges 123 are formed integrally with the cassette body 51. However, the raised projections 119 and ledges 123 can be formed separately from the cassette body 51 and attached to the cassette body in a suitable fashion. To detach the cassette 5 from the pump housing 3, the tab 125 can be depressed to disengage the ledges 123 from the catch 127.

Once the cassette 5 is attached to the pump housing 3, the tube 45 of the feeding set 7 is positioned for engagement by the rollers 43 of the pump 1. The rollers 43 engage the tube 45 at portions of the tube supported by the flexible stator member 113. Engagement of the tube 45 by a roller 43 causes the flexible stator member 113 to flex or move away from the roller. In particular, the movement allows the tube 45 to at least partially straighten out into a more linear configuration permitting the rollers 43 to occlude the tube in a semi-linear fashion. Therefore, instead of pulling and stretching the tube 45 as can be the case with rollers in conventional pumps, the rollers 43 slide along the tube and occlude the tube in a reduced tension state. As a result, the rollers 43 produce aliquots consistent with the actual linear dimensions of the tube 45. Accordingly, the calculated aliquot volume of the pump 1 more closely matches the actual aliquot volume produced by the pump resulting in more accurate feeding.

Referring to FIGS. 14-17, a pump set of another embodiment is generally indicated at 7'. The pump set comprises a cassette 5' including a cassette body 51', a fitting assembly 82' including a fitting 65' received in the cassette body and a stem 68' movably received in the fitting, and a tube 45' attached to the fitting. The cassette 5' is similar to the cassette of the first embodiment except for the configuration of the fitting 65', and in particular, the second attachment portion 81' of the outlet 71' of the fitting. In this embodiment, the second attachment portion 81' extends laterally away from the inlet 69' and extends through a notch 102' in a side wall 61' of the cassette 5'. Outlet tubing 83' is received in the second attachment portion 81' and extends laterally away from the housing 51' of the cassette 5'. The laterally extending outlet tubing 83' provides an orientation that resists kinking better than an outlet tube extending vertically upward from the second attachment portion 81'. This is because the downward force created by fluid flowing through the outlet tubing 83' will cause less of a bend in the laterally extending outlet tubing reducing the chances of a kink being formed. Also, because the outlet tubing 83' generally bends downward from the cassette 5' to reach the patient, having the outlet tubing extend laterally from the cassette orients the tubing in a position that is better suited for reaching the patient without the weight of the fluid causing the tubing to kink.

Referring to FIGS. 18-21, a pump set of another embodiment is generally indicated at 7". The pump set comprises a cassette 5" including a cassette body 51", a fitting assembly 82" including a fitting 65" received in the cassette body and a stem 68" movably received in the fitting, and a tube 45" attached to the fitting. The cassette 5" is similar to the cassette of the previous embodiments except for the configuration of the fitting 65", and in particular, the outlet 71" of the fitting. In this embodiment, the outlet 71" comprises an angled arch shaped portion 104" and a flow guide 106" received in the arch-shaped portion. The flow guide 106" has an open top which is closed by the arch shaped portion 104" providing an arched flow passage through the outlet 71" of the fitting 65". A downstream portion of the tube 45" connects to a first attachment portion 79" of the flow guide 106" and a second attachment portion 81" of the flow guide connects to outlet tubing 83". Because of the arched shape of the outlet 71", the second attachment portion 81" extends downward through an opening 102" in the front 53" of the cassette 5". Outlet tubing 83" is received in the second attachment portion 81" and extends downward adjacent the front 53" of the housing 51" of the cassette 5". The downwardly extending outlet tubing 83" provides an orientation that resists kinking better than an outlet tube extending vertically upward from the second attachment portion 81". This is because the downward force created by fluid flowing through the outlet tubing 83" will cause less of a bend in the already downwardly extending outlet tubing reducing the chances of a kink being formed. Also, because the outlet tubing 83" generally has to bend down from the cassette 5" to reach the patient, having the outlet tubing already extending downward from the cassette orients the tubing in a position that is better suited for reaching the patient without the weight of the fluid causing the tubing to kink.

Referring to FIGS. 22-25, a pump set of another embodiment is generally indicated at 7". The pump set comprises a cassette 5'" including a cassette body 51'", a fitting assembly 82" including a fitting 65'" received in the cassette body and a stem 68" movably received in the fitting, and a tube 45'" attached to the fitting. The cassette 5'" is similar to the cassette of the previous embodiments except for the configuration of the fitting 65'", and in particular, the outlet 71'" of the fitting. In this embodiment, the outlet 71'" comprises an arch shaped portion 104'" and a flow guide 106'" received over the arch shaped portion. The arch shaped portion 104'" has an open top which is closed by the flow guide 106'" providing an arched flow passage through the outlet 71'" of the fitting 65". A downstream portion of the tube 45" connects to a first attachment portion 79" of the arch shaped portion 104'" and a second attachment portion 81'" of the arch shaped portion connects to outlet tubing 83". Because of the arched shape of the outlet 71", the second attachment portion 81'" extends downward through an opening (not shown) in a side projection of the cassette 5'". Outlet tubing 83" is received in the second attachment portion 81" and extends downward adjacent a side wall 61'" of the cassette 5". The downwardly extending outlet tubing 83'" provides an orientation that resists kinking better than an outlet tube extending vertically upward from the second attachment portion 81'". This is because the downward force created by fluid flowing through the outlet tubing 83" will cause less of a bend in the already downwardly extending outlet tubing reducing the chances of a kink being formed. Also, because the outlet tubing 83'" generally has to bend down from the cassette 5'" to reach the patient, having the outlet tubing already extending downward from the cassette orients the tubing in a position that is better suited for reaching the patient without the weight of the fluid causing the tubing to kink.

In one, nonexclusive statement of the invention, a cassette for use with a pumping apparatus generally comprises a body configured for releasable attachment to the pumping apparatus to mount the cassette to the pumping apparatus. The body comprises a front, a back, a top, a bottom, and a curved guide wall extending downward from the top of body. A fitting mounted on the body has an inlet port for attaching inlet tubing to the cassette and an outlet port for attaching outlet tubing to the cassette. The outlet port is recessed from the top of the body, and the curved guide wall extends adjacent the outlet port of the fitting for supporting the outlet tubing to prevent kinking of the outlet tubing.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed:

1. A pump set for use with a pumping apparatus, the pump set comprising:
    tubing for carrying a liquid, the tubing comprising an inlet section for connection to a liquid source and a pump engagement section configured for engagement by the pumping apparatus to pump the liquid through the tubing; and
    a valve mechanism attached to the tubing between the inlet section and the pump engagement section, the valve mechanism comprising a first port connected to the inlet section of the tubing, a second port connected to the pump engagement section of the tubing, and a valve disposed between the first and second ports, the valve including a rotatable stem to selectively communicate the first port with the second port, the stem including a flow passage extending through the stem from an inlet end of the flow passage to an outlet end of the flow passage whereby the inlet end of the flow passage communicates with the first port and the outlet end of the flow passage communicates with the second port to place the inlet section of the tubing in communication with the pump engagement section of the tubing, the flow passage increasing in cross-sectional area from the inlet end toward the outlet end, wherein the cross-sectional area of the flow passage changes at different rates through the flow passage from the inlet end to the outlet end,
    wherein the flow passage includes a first section and a second section, the first section extending from the inlet end toward the outlet end, the first section widening as the first section extends from the inlet end, the second section extending from the first section toward the outlet end, the second section widening at a rate different from the first section as the second section extends from the first section toward the outlet end.

2. A pump set as set forth in claim 1, wherein a maximum rate of increase in the cross-sectional area of the flow passage occurs generally intermediate the inlet end and outlet end of the flow passage.

3. A pump set as set forth in claim 1, wherein the flow passage includes a third section extending from the second section toward the outlet end the third section widening at a rate different from the second section as the third section extends from the second section toward the outlet end.

4. A pump set as set forth in claim 3, wherein the flow passage includes a fourth section extending from the third section to the outlet end, the fourth section widening at a rate different from the third section as the fourth section extends from the third section to the outlet end.

5. A pump set as set forth in claim 1, wherein the tubing comprises a first tubing for connection to a first liquid source and a second tubing for connection to a second liquid source, the first port being connected to the first tubing, the valve mechanism comprising a third port connected to a third tubing, the stem being rotatably mounted to selectively communicate the outlet end of the flow passage with the first and third ports, the outlet end of the flow passage remaining in communication with the second port when the inlet end is rotated between the first and third ports.

6. A pump set as set forth in claim 5, wherein longitudinal axes of the first port, second port, third port and flow passage are generally coplanar.

7. A pump set as set forth in claim 1, further comprising a cassette configured for releasable attachment to the pumping apparatus, the tubing and the valve mechanism being releasably mounted to the cassette.

8. A pump set as set forth in claim 1, wherein the first port has a non-uniformly circular-shaped opening for communicating liquid to the flow passage in the valve stem.

9. A pump set as set forth in claim 1, wherein the valve includes a stem holder for mounting the stem, the stem holder defining stops positioned to be engaged by a flange of the stem to limit rotation of the stem in the stem holder.

10. A pump set as set forth in claim 9, wherein the stem holder has a recessed portion configured to receive a catch when attached to the pumping apparatus.

11. A pump set as set forth in claim 9, wherein the flange projects radially outward from the stem.

12. A pump set as set forth in claim 11, wherein the flange has a generally fan shape that extends radially around the stem.

13. A fitting assembly for use in a cassette configured for attachment to a pumping apparatus, the fitting assembly comprising:
a first port,
a second port, and
a valve disposed between the first and second ports, the valve including a stem rotatably mounted to selectively communicate the first port with the second port, the stem including a flow passage extending through the stem from an inlet end of the flow passage to an outlet end of the flow passage whereby the inlet end of the flow passage communicates with the first port and the outlet end of the flow passage communicates with the second port to place an inlet section of tubing in communication with a pump engagement section of the tubing, the flow passage increasing in cross-sectional area from the inlet end toward the outlet end, wherein the cross-sectional area of the flow passage changes at different rates through the flow passage from the inlet end to the outlet end, and
the cassette comprising:
a body configured for releasable attachment to the pumping apparatus to mount the cassette to the pumping apparatus; and
a fitting releasably mountable to the body, the fitting including a valve mechanism comprising the first port, the second port, and the valve disposed between the first and second ports, the valve including the stem rotatably mounted to selectively communicate the first port with the second port, the stem including a flange to secure the fitting to the pumping apparatus when the stem is rotated to communicate the first port with the second port.

14. A fitting assembly as set forth in claim 13, wherein the tubing and the valve mechanism being releasably mounted to the cassette.

15. A fitting assembly as set forth in claim 13, wherein a maximum rate of increase in the cross-sectional area of the flow passage occurs generally intermediate the inlet end and outlet end of the flow passage.

16. A fitting assembly as set forth in claim 15, wherein the first port has a non-uniformly circular-shaped opening for communicating liquid to the flow passage in the valve stem.

17. A fitting assembly as set forth in claim 13, wherein the flow passage includes a first section extending from the inlet end toward the outlet end, the first section widening as the first section extends from the inlet end.

18. A fitting assembly as set forth in claim 17, wherein the flow passage includes a second section extending from the first section toward the outlet end, the second section widening at a rate different from the first section as the second section extends from the first section toward the outlet end.

19. A fitting assembly as set forth in claim 18, wherein the flow passage includes a third section extending from the second section toward the outlet end the third section widening at a rate different from the second section as the third section extends from the second section toward the outlet end.

20. A fitting assembly as set forth in claim 19, wherein the flow passage includes a fourth section extending from the third section to the outlet end, the fourth section widening at a rate different from the third section as the fourth section extends from the third section to the outlet end.

21. A fitting assembly as set forth in claim 13, wherein the valve includes a stem holder for mounting the stem, the stem holder defining stops positioned to be engaged by the flange to limit rotation of the stem in the stem holder.

22. A fitting assembly as set forth in claim 21, wherein the stem holder has a recessed portion configured to receive a catch when the body is attached to the pumping apparatus.

23. A fitting assembly as set forth in claim 13, wherein the flange projects radially outward from the stem.

24. A fitting assembly as set forth in claim 23, wherein the flange has a generally fan shape that extends radially around the stem.

25. A pump set for use with a pumping apparatus, comprising:
tubing for carrying a liquid, the tubing comprising an inlet section for connection to a liquid source and a pump engagement section configured for engagement by the pumping apparatus to pump the liquid through the tubing;
a valve mechanism attached to the tubing between the inlet section and the pump engagement section, the valve mechanism comprising a first port connected to the inlet section of the tubing, a second port connected to the pump engagement section of the tubing, and a valve disposed between the first and second ports, the valve including a rotatable stem to selectively communicate the first port with the second port, the stem including a flow passage extending through the stem from an inlet end of the flow passage to an outlet end of the flow passage whereby the inlet end of the flow passage communicates with the first port and the outlet end of the flow passage communicates with the second port to place the inlet section of the tubing in communication with the pump engagement section of the tubing, the flow passage increasing in cross-sectional area from the inlet end toward the outlet end, wherein the cross-sectional area of the flow passage changes at different rates through the flow passage from the inlet end to the outlet end; and a cassette for use with the pumping apparatus, the cassette comprising:

a body configured for releasable attachment to the pumping apparatus to mount the cassette to the pumping apparatus; and a fitting releasably mountable to the body, the fitting including the valve mechanism comprising the first port, the second port, and the valve disposed between the first and second ports, the valve including the stem rotatably mounted to selectively communicate the first port with the second port, the stem including a flange to secure the fitting to the pumping apparatus when the stem is rotated to communicate the first port with the second port.

26. A pump set as set forth in claim 25, wherein the valve includes a stem holder for mounting the stem, the stem holder defining stops positioned to be engaged by the flange to limit rotation of the stem in the stem holder.

27. A pump set as set forth in claim 26, wherein the stem holder has a recessed portion configured to receive a catch when the body is attached to the pumping apparatus.

28. A pump set as set forth in claim 25, wherein the flange projects radially outward from the stem.

29. A pump set as set forth in claim 28, wherein the flange has a generally fan shape that extends radially around the stem.

30. A pump set as set forth in claim 25, wherein a maximum rate of increase in the cross-sectional area of the flow passage occurs generally intermediate the inlet end and outlet end of the flow passage.

31. A pump set as set forth in claim 25, wherein the flow passage includes a first section extending from the inlet end toward the outlet end, the first section widening as the first section extends from the inlet end.

32. A pump set as set forth in claim 31, wherein the flow passage includes a second section extending from the first section toward the outlet end, the second section widening at a rate different from the first section as the second section extends from the first section toward the outlet end.

33. A pump set as set forth in claim 32, wherein the flow passage includes a third section extending from the second section toward the outlet end, the third section widening at a rate different from the second section as the third section extends from the second section toward the outlet end.

34. A pump set as set forth in claim 33, wherein the flow passage includes a fourth section extending from the third section to the outlet end, the fourth section widening at a rate different from the third section as the fourth section extends from the third section to the outlet end.

35. A pump set as set forth in claim 25, wherein the tubing and the valve mechanism being releasably mounted to the cassette.

36. A pump set as set forth in claim 25, wherein the first port has a non-uniformly circular-shaped opening for communicating liquid to the flow passage in the valve stem.

* * * * *